US012254986B2

(12) United States Patent
Martin et al.

(10) Patent No.: US 12,254,986 B2
(45) Date of Patent: Mar. 18, 2025

(54) INTERACTION ANALYSIS

(71) Applicant: IESO DIGITAL HEALTH LIMITED, Cambridge (GB)

(72) Inventors: Alan James Martin, Cambridge (GB); Mihai Valentin Tablan, Cambridge (GB); Andrew Damian Blackwell, Cambridge (GB)

(73) Assignee: IESO DIGITAL HEALTH LIMITED, Cambridge (GB)

( * ) Notice: Subject to any disclaimer, the term of this patent is extended or adjusted under 35 U.S.C. 154(b) by 361 days.

(21) Appl. No.: 17/642,152

(22) PCT Filed: Sep. 25, 2020

(86) PCT No.: PCT/GB2020/052334
§ 371 (c)(1),
(2) Date: Mar. 10, 2022

(87) PCT Pub. No.: WO2021/058978
PCT Pub. Date: Apr. 1, 2021

(65) Prior Publication Data
US 2022/0384038 A1   Dec. 1, 2022

(30) Foreign Application Priority Data
Sep. 26, 2019   (GB) ..................... 1913908

(51) Int. Cl.
*G16H 50/20*   (2018.01)
*G06F 16/35*   (2019.01)
(Continued)

(52) U.S. Cl.
CPC ............. *G16H 50/20* (2018.01); *G06F 16/35* (2019.01); *G06F 40/30* (2020.01); *G16H 20/70* (2018.01)

(58) Field of Classification Search
CPC ........ G16H 50/20; G16H 20/70; G06F 16/35; G06F 40/30
See application file for complete search history.

(56) References Cited

U.S. PATENT DOCUMENTS

| 2012/0232930 | A1* | 9/2012 | Schmidt | G16H 50/20 705/3 |
| 2014/0089003 | A1* | 3/2014 | Frey | G16H 50/70 705/3 |
| 2016/0012341 | A1* | 1/2016 | Raman | G16H 50/70 706/51 |

FOREIGN PATENT DOCUMENTS

WO   WO-2016071659 A1 *   5/2016   ............. A61B 5/165

OTHER PUBLICATIONS

Shen, Chenlin, et al. "Sentiment classification towards question-answering with hierarchical matching network." Proceedings of the 2018 Conference on Empirical Methods in Natural Language Processing. 2018. (Year: 2018).*

(Continued)

*Primary Examiner* — Anne L Thomas-Homescu
(74) *Attorney, Agent, or Firm* — ALSTON & BIRD LLP

(57) ABSTRACT

A computer-implemented method of analysing transcript data, comprising: receiving a plurality of transcripts and a set of outcome data for each transcript, the outcome data associating each transcript with one or more outcomes; receiving a query transcript; processing the query transcript and each transcript within the plurality of transcripts; comparing, the processed data representing the query transcript with the processed data representing the plurality of transcripts, to identify a subset of the plurality of transcripts that meet a threshold similarity criterion with respect to the query transcript; and thereby determining a relationship between the query transcript and one or more outcomes.

21 Claims, 11 Drawing Sheets

(51) Int. Cl.
*G06F 40/30* (2020.01)
*G16H 20/70* (2018.01)

(56) References Cited

OTHER PUBLICATIONS

International Search Report and Written Opinion for corresponding PCT application PCT/GB2020/052334, dated Dec. 21, 2020.

* cited by examiner

INTERACTION ANALYSIS

FIELD OF THE INVENTION

This invention relates to the analysis of transcript data, where a transcript relates to an interaction between two or more parties. Based on the analysis, a relationship is determined between the transcript data and one or more potential outcomes of the interaction, based on known outcomes of other transcripts relating to other interactions. Where the transcript data relates to psychotherapy, the method can be used to determine the dose of psychotherapy delivered. The invention also relates to a system, and computer-readable storage medium for carrying out the methods.

BACKGROUND OF THE INVENTION

Interactions between two or more parties, even within a well-defined domain, can be highly variable, and the variation between different interactions can have a material effect on their outcome. Where the outcome of an interaction is important or of value, such as in a clinician/patient interaction, a salesperson/customer interaction, or an educator/student interaction, the ability to analyse an interaction in an unbiased, repeatable manner permits the mitigation of these differences and therefore has a positive effect on outcome.

One such interaction is that between a clinician or a provider of therapy (a therapist, a therapy agent) and a patient, for example a patient suffering from a mental health disorder. Common mental health disorders including depression and anxiety are characterized by intense emotional distress, which affects social and occupational functioning. About one in four adults worldwide suffer from a mental health problem in any given year. In the US, mental disorders are associated with estimated direct health system costs of $201 billion per year, growing at a rate of 6% per year, faster than the gross domestic product growth rate of 4% per year. Combined with annual loss of earnings of $193 billion, the estimated total mental health cost is at almost $400 billion per year. In the UK mental health disorders are associated with service costs of £22.5 billion per year and annual loss of earnings of £26.1 billion.

Various treatment options for common mental health disorders are available; as well as or instead of medication, these may include psychotherapy including: traditional cognitive behavioral therapy (CBT), computerised or online CBT, internet-enabled CBT (IECBT), and digital therapeutics. A computer-based system for providing internet-enabled CBT is described in WO 2016/071660 A1 (which is hereby incorporated by reference). Amongst other things, the system enables patients and therapists to exchange messages, particularly text-based messages, during sessions and courses of therapy.

Compared to the treatment of physical conditions, the average quality of care of mental health disorders remains poor and the rate of improvement in treatment is slow. Outcomes for many mental health disorders have stagnated since the original treatments were developed and in some cases the efficacy of psychotherapy appears to be reducing overtime. Improving the effectiveness of treatment for any disorder is dependent upon accurate measurement of treatment delivery and an understanding of how the treatment works. Whilst it is relatively simple to monitor and measure the delivery of most medical treatments (e.g. the dosage of a prescribed medication given), monitoring the delivery of (psycho)therapy (i.e. determining the 'dose' of psychotherapy delivered) is a significantly greater challenge.

The interaction between a therapist and a patient during one-to-one therapy is a very important part of the therapy process. Little is currently known about the variability between different therapist-patient interactions, for example variability between the therapy delivered in different therapy sessions; furthermore little is known about how this variability impacts the quality or efficacy of the therapy, i.e. the likelihood of a patient engaging, improving or recovering. These, and other interactions between at least two parties, are difficult to analyse, improve or control. A computer-implemented method of measuring the delivery of therapy is described in international application PCT/GB2019/051380 (which is hereby incorporated by reference). PCT/GB2019/051380 describes a computer-implemented method of dividing the transcript of a therapy session into a plurality of utterances, assigning a semantic representation from one of a limited number of categories to each of the utterances based on their content, and using the assigned semantic representations to form a representation of the therapy session, thereby providing a measure of the therapy delivered in that session.

However, as stated above, therapy sessions, like other interactions between two parties, are highly variable. The methods disclosed in PCT/GB2019/051380 are based on measures of the quantity of utterances of particular types that occur in therapy sessions. Two or more therapy sessions may contain the same quantity of utterances of particular types, but still be highly variable relative to each other, with that variability leading to differences in quality and outcome of the therapy delivered.

For these reasons, a new approach is required to improve, augment or assist with measuring/evaluating the content of therapy sessions in an unbiased, repeatable manner.

SUMMARY OF THE INVENTION

According to one aspect of the present invention, there is provided a computer-implemented method of analysing transcript data, the method comprising: receiving a plurality of transcripts and a set of outcome data for each transcript, the outcome data associating each transcript with one or more outcomes; receiving a query transcript; processing the query transcript and each transcript within the plurality of transcripts, wherein processing comprises: segmenting each transcript into a sequence of utterances; classifying each utterance as corresponding to one or more categories from a predetermined list of categories; and tagging each utterance with one or more of the categories such that each transcript is readable as a sequence of categories; comparing, using a fuzzy sequence matching algorithm, the sequence of categories representing the query transcript with the sequences of categories each representing one of the plurality of transcripts, to identify a subset of the sequences of categories representing the plurality of transcripts that contain one or more sub-sequences of categories which meet a threshold similarity criterion with respect to one or more sub-sequences of categories contained in the sequence of categories representing the query transcript; and determining a relationship between each of the one or more sub-sequences of categories contained in the sequence of categories representing the query transcript and one or more outcomes, based on the outcome data associated with the transcripts relating to the identified subset of the sequences of categories representing the plurality of transcripts.

According to another aspect of the present invention, there is provided a computer-implemented method of analysing transcript data, the method comprising receiving a plurality of transcripts and a set of outcome data for each transcript, the outcome data associating each transcript with one or more outcomes, receiving a query transcript, and processing each transcript, wherein the processing comprises the steps of segmenting the transcript into a sequence of utterances, classifying each utterance as corresponding to one or more categories from a predetermined list of categories, and tagging each category such that the transcript can be read as a sequence of categories. The method further comprising comparing, using a fuzzy sequence matching algorithm, the query transcript with each of the plurality of transcripts to identify a subset of the plurality of transcripts containing one or more sub-sequences of categories which meet a threshold similarity criterion with respect to one or more sub-sequences of categories contained in the query transcript and determining, for each of the one or more sub-sequences of categories in the query transcript, a relationship between that sub-sequence of categories and one or more outcomes based on the outcome data for the identified subset.

Transcript data analysed may be transcript data of written or spoken conversations or dialogues.

Applying a local sequencing alignment algorithm to transcripts having associated outcome data enables associations to be determined between repeating portions of those transcripts and a given outcome. This pattern recognition is automated, and thus allows for actionable insights to be gained from vast datasets very quickly, and for predictions to be made based on new transcripts having no associated outcome data. The method of the present invention may provide such advantages in any case where a relatively large set of transcripts is available, each of which can be linked to one or more outcomes. For example, the present application may have applications in sales, education, and in particular in therapy.

In some embodiments of any aspect of the invention, the matching algorithm is a local sequence alignment algorithm.

In particular, in some embodiments of any aspect of the invention, the local sequence alignment algorithm is a Smith Waterman Local Alignment algorithm.

In such embodiments, the sub-sequences of categories from the query transcript may be obtained by generating a scoring matrix between the query transcript and each of the plurality of transcripts.

Suitably, the sub-sequences of categories contained in the sequence of categories representing the query transcript are obtained by generating a scoring matrix between the sequence of categories representing the query transcript and the sequences of categories each representing one of the plurality of transcripts.

Using a scoring matrix for match identification and sub-sequence comparison ensures that sub-sequences of any length within a predetermined range are found, if they meet the similarity threshold.

Suitably, the threshold similarity criterion is met if a sub-sequence of categories contained in the sequence of categories representing the query transcript and a sub-sequence of categories contained in one of the sequences of categories representing the plurality of transcripts produce a score in the scoring matrix which is equal to or greater than a predetermined cutoff score.

Furthermore, in some embodiments the threshold similarity criterion may be met if a sub-sequence of categories from the query transcript and a sub-sequence of categories from one of the plurality of transcripts produce a score in the scoring matrix which is equal to or greater than a predetermined cutoff score.

Furthermore, in some embodiments, the method may further comprise setting one or more parameters to define the manner in which the scoring matrix is generated, the one or more parameters comprising one or more of: a match score, a mismatch cost, and a gap cost.

In other embodiments, the local sequence alignment algorithm is a basic local alignment search tool (BLAST) algorithm.

In some embodiments the sub-sequences of categories from the query transcript may be obtained by dividing the transcript into overlapping n-grams, each n-gram comprising n categories. In some embodiments, the sub-sequences of categories contained in the sequence of categories representing the query transcript are obtained by dividing the sequence of categories representing the query transcript into overlapping n-grams, each n-gram comprising n categories.

Dividing transcripts into overlapping n-grams allows for a flexible comparison tool which is unbiased and agnostic in terms of the input data.

In some embodiments, determining the relationship comprises determining a strength of correlation or anti-correlation between each sub-sequence of categories from the query transcript and each of the one or more outcomes. In some embodiments, determining the relationship comprises determining a strength of correlation or anti-correlation between each sub-sequence of categories contained in the sequence of categories representing the query transcript and each of the one or more outcomes.

Determining a strength of correlation/anti-correlation between a sub-sequence of categories and a given outcome enables analysis of which category sub-sequences are more or less likely to achieve a desired effect.

In some embodiments, the method further comprises assigning a credible interval to the relationship determined between each sub-sequence of categories from the query transcript and each of the one or more outcomes, the credible interval being determined based at least in part on the number and/or proportion of the subset of transcripts containing the given sub-sequence of categories and that are associated with a given outcome. In some embodiments, the method further comprises assigning a credible interval to the relationship determined between each sub-sequence of categories contained in the sequence of categories representing the query transcript and each of the one or more outcomes; wherein the credible interval is determined based at least in part on the number and/or proportion of the sequences of categories representing the plurality of transcripts that contain each sub-sequence of categories and that are associated with each of the one or more outcomes.

Credible intervals are an additional statistical tool, analogous to confidence intervals, useful in interpreting insights gained from large data sets, and the method of the present invention allows this information to be generated and linked to the determined relationships easily.

In some embodiments, the transcript data is therapy transcript data, preferably psychotherapy transcript data. Applying the method of the present invention to therapy transcripts allows for effective therapy regimes to be determined.

In some embodiments, the transcript data comprises a transcript of an interaction between a therapist and a patient for one or more therapy sessions. This allows for individual therapy sessions to be assessed for effective or ineffective patterns, for individual therapists to be assessed, and for factors such as the severity of a patient's problem to be factored into analysis.

The interaction between a therapist and a patient may occur during a discrete, finite time-frame such as a scheduled therapy session, either in person (face-to-face), via a voice or voice and video service, or an instant text-based interaction, or may occur more intermittently over a longer time-frame, such as a would be expected to occur during instant or non-instant messaging or any other suitable method. Suitably, transcript data may therefore comprise a transcript of any of these types of interaction.

In some embodiments, the transcript data is gathered by one or more of: a written conversation between therapist and patient, translation of a spoken conversation to a textual form, suitably using speech recognition software. In some embodiments, the transcript data is gathered by one or more of: a written conversation between therapist and patient, translation of a spoken conversation to a textual form, suitably using speech recognition software. In some embodiments, the transcript data is gathered by one or more of: recording a written conversation between two or more parties, translating a spoken conversation to a textual form using speech recognition software.

In some embodiments, a therapist is a human therapist or a human therapy agent, e.g. a person trained to deliver therapy. In other embodiments, a therapist is a digital therapist or a digital therapy agent.

In some embodiments, the one or more outcomes include one or more of: patient recovery, patient improvement and patient engagement. Prediction of such outcomes and knowledge of how to encourage them is a crucial part of determining effective therapy regimes.

In some embodiments, the method further comprises classifying the one or more sub-sequences of categories from the query transcript as effective therapy or ineffective therapy based on the determined relationships.

In some embodiments, the method further comprises assessing the dose of therapy for the query transcript based on the relative frequency of sub-sequences classified as effective and ineffective.

In some embodiments, the predetermined list of categories comprises categories relating to types of therapeutic dialogue.

In some embodiments, the predetermined list of categories comprises categories suitable for the type of transcript data being analysed. For example where the transcript data relates to an education interaction, the predetermined list of categories may comprise categories relating to education, alternatively where the transcript data relates to a sales interaction, the predetermined list of categories may comprise categories relating to sales. The categories may be termed in-domain categories, and may be determined by any suitable method.

According to another aspect, there is provided computer-implemented method of determining the dose of psychotherapy delivered during a query psychotherapy interaction, the method comprising: receiving a plurality of psychotherapy interaction transcripts and a set of outcome data for each transcript, the outcome data associating each transcript with one or more outcomes; receiving a query psychotherapy interaction transcript; processing the query transcript and each transcript within the plurality of transcripts, wherein processing comprises: segmenting each transcript into a sequence of utterances; classifying each utterance as corresponding to one or more categories from a predetermined list of categories; and tagging each utterance with one or more of the categories such that each transcript is readable as a sequence of categories; comparing, using a fuzzy sequence matching algorithm, the sequence of categories representing the query transcript with the sequences of categories each representing one of the plurality of transcripts, to identify a subset of the sequences of categories representing the plurality of transcripts that contain one or more sub-sequences of categories which meet a threshold similarity criterion with respect to one or more sub-sequences of categories contained in the sequence of categories representing the query transcript; and determining a relationship between each of the one or more sub-sequences of categories contained in the sequence of categories representing the query transcript and an outcome, based on the outcome data associated with the transcripts relating to the identified subset of the sequences of categories representing the plurality of transcripts; and determining the dose of psychotherapy delivered during the query psychotherapy interaction by combining the outcomes relating to the one or more sub-sequences relating to the query transcript.

Combining the outcomes relating to the one or more sub-sequences relating to the query transcript may be performed in any suitable way.

According to another aspect, there is provided a system configured to carry out the method of the present invention, the system comprising: a processing unit; a memory unit; and a computer-readable storage medium comprising instructions which, when executed by the processing unit, cause the processing unit to carry out the method of the present invention.

According to another aspect of the present invention, there is provided a system configured to analyse transcript data, comprising: a processing unit; a memory unit; and a computer-readable storage medium comprising instructions which, when executed by the processing unit, cause the processing unit to: receive a plurality of transcripts and a set of outcome data for each transcript, the outcome data associating each transcript with one or more outcomes; receive a query transcript; process the query transcript and each transcript within the plurality of transcripts by: segmenting each transcript into a sequence of utterances; and classifying each utterance as corresponding to one or more categories from a predetermined list of categories; and tagging each utterance with one or more of the categories such that each transcript is readable as a sequence of categories; compare, using a fuzzy sequence matching algorithm, the sequence of categories representing the query transcript with the sequences of categories each representing one of the plurality of transcripts, to identify a subset of the sequences of categories representing the plurality of transcripts that contain one or more sub-sequences of categories which meet a threshold similarity criterion with respect to one or more sub-sequences of categories contained in the sequence of categories representing the query transcript; and determine a relationship between each of the one or more sub-sequences of categories contained in the sequence of categories representing the query transcript and one or more outcomes, based on the outcome data associated with the transcripts relating to the identified subset of the sequences of categories representing the plurality of transcripts.

According to another aspect of the present invention, there is provided a system configured to determine the dose of psychotherapy delivered during a query psychotherapy interaction, comprising: a processing unit; a memory unit; and a computer-readable storage medium comprising instructions which, when executed by the processing unit, cause the processing unit to: receive a plurality of psychotherapy interaction transcripts and a set of outcome data for each transcript, the outcome data associating each transcript with one or more outcomes; receive a query psychotherapy interaction transcript; process the query transcript and each transcript within the plurality of transcripts, wherein processing comprises: segmenting each transcript into a sequence of utterances; classifying each utterance as corresponding to one or more categories from a predetermined list of categories; and tagging each utterance with one or more of the categories such that each transcript is readable as a sequence of categories; compare, using a fuzzy sequence matching algorithm, the sequence of categories representing the query transcript with the sequences of categories each representing one of the plurality of transcripts, to identify a subset of the sequences of categories representing the plurality of transcripts that contain one or more sub-sequences of categories which meet a threshold similarity criterion with respect to one or more sub-sequences of categories contained in the sequence of categories representing the query transcript; determine a relationship between each of the one or more sub-sequences of categories contained in the sequence of categories representing the query transcript and an outcome, based on the outcome data associated with the transcripts relating to the identified subset of the sequences of categories representing the plurality of transcripts; and determine the dose of psychotherapy delivered during the query psychotherapy interaction by combining the outcomes relating to the one or more sub-sequences relating to the query transcript. According to another aspect of the present invention, there is provided a computer-readable storage medium comprising instructions which, when executed by a processor, cause the processor to carry out the method of the present invention.

According to another aspect of the present invention, there is provided a computer-readable storage medium comprising instructions which, when executed by a processor, cause the processor to: receive a plurality of transcripts and a set of outcome data for each transcript, the outcome data associating each transcript with one or more outcomes; receive a query transcript; process the query transcript and each transcript within the plurality of transcripts by: segmenting each transcript into a sequence of utterances; and classifying each utterance as corresponding to one or more categories from a predetermined list of categories; and tagging each utterance with one or more of the categories such that each transcript is readable as a sequence of categories; compare, using a fuzzy sequence matching algorithm, the sequence of categories representing the query transcript with the sequences of categories each representing one of the plurality of transcripts, to identify a subset of the sequences of categories representing the plurality of transcripts that contain one or more sub-sequences of categories which meet a threshold similarity criterion with respect to one or more sub-sequences of categories contained in the sequence of categories representing the query transcript; and determine a relationship between each of the one or more sub-sequences of categories contained in the sequence of categories representing the query transcript and one or more outcomes, based on the outcome data associated with the transcripts relating to the identified subset of the sequences of categories representing the plurality of transcripts.

According to another aspect of the present invention, there is provided a computer-readable storage medium comprising instructions which, when executed by a processor, cause the processor to: receive a plurality of psychotherapy interaction transcripts and a set of outcome data for each transcript, the outcome data associating each transcript with one or more outcomes; receive a query psychotherapy interaction transcript; process the query transcript and each transcript within the plurality of transcripts, wherein processing comprises: segmenting each transcript into a sequence of utterances; classifying each utterance as corresponding to one or more categories from a predetermined list of categories; and tagging each utterance with one or more of the categories such that each transcript is readable as a sequence of categories; compare, using a fuzzy sequence matching algorithm, the sequence of categories representing the query transcript with the sequences of categories each representing one of the plurality of transcripts, to identify a subset of the sequences of categories representing the plurality of transcripts that contain one or more sub-sequences of categories which meet a threshold similarity criterion with respect to one or more sub-sequences of categories contained in the sequence of categories representing the query transcript; determine a relationship between each of the one or more sub-sequences of categories contained in the sequence of categories representing the query transcript and an outcome, based on the outcome data associated with the transcripts relating to the identified subset of the sequences of categories representing the plurality of transcripts; and determine the dose of psychotherapy delivered during the query psychotherapy interaction by combining the outcomes relating to the one or more sub-sequences relating to the query transcript.

Unless specifically stated, a process or method comprising steps may be performed in any suitable order. Thus steps can be performed in any appropriate order, including contemporaneously. The same applies to any system configured to carry out the method(s) of the present invention, or to any instructions comprised on a computer-readable storage medium provided to cause a processor to carry out the method of the present invention. Improving quality of care of mental health disorders and improving the efficacy of psychotherapy requires that treatment be delivered as intended, however monitoring and quantifying the delivery of psychotherapy was heretofore a substantial challenge.

The systems and methods of the invention may therefore be used to improve the quality of therapy delivered to patients, and thereby improve patient outcome (likelihood of improvement or recovery, likelihood of engagement). The invention may also be used to improve and refine the therapy delivered to particular patient groups, thereby providing differentiated healthcare (personalised medicine). By improving and refining the therapy delivered, patients may be more likely to improve and/or recover, and may require fewer sessions of therapy. This is beneficial to the patient in terms of time, convenience, cost (both of monetary cost of therapy, and also reduced cost from e.g. time off work), and is also beneficial to the therapist or healthcare service in terms of increasing the numbers of patients treatable in a given time, reducing overheads per patient, and increasing profit in a pay-for-value payment model.

The systems and methods described herein represent a new approach for quality controlled behavioral health care. For example, the approach described herein provides a method of monitoring therapists' performance. 'Therapist drift'—the failure to deliver treatments that a therapist has been trained to deliver—is considered one of the biggest factors contributing to poor delivery of evidence based treatment (G. Waller, Evidence-based treatment and therapist drift. *Behav. Res. Ther.* 47, 119-127 (2009)). Automated monitoring of therapists' performance could help prevent therapist drift and associated lower improvement rate, phenomena that have been particularly noted in the case of more experienced therapists. The approach described herein could also be applied to monitor and inform the practice of face-to-face psychotherapy; methods to capture and categorise face-to-face session content through the use of automatic speech recognition software are in development.

A major factor thought to underlie therapist drift is the increase in the confidence a therapist develops over time in their own knowledge above that of therapeutic guidelines (G. Waller, H. Turner, Therapist drift redux: Why well-meaning clinicians fail to deliver evidence-based therapy, and how to get back on track. Behav. Res. Ther. (2016), doi:10.1016/j.brat.2015.12.005). The aspects of the invention described herein provide valuable improvements over traditional therapy, therapy monitoring and consequent actions, for example by reducing the incidence of therapist drift.

DETAILED DESCRIPTION OF THE INVENTION

The invention relates to computer-implemented methods, systems, computer-readable storage media and computer program products that provide insights into the content of transcript data. Where the transcript data relates to an interaction between a therapist and a patient, for example a patient with a mental health disorder, uses of those insights include data-driven improvement of the treatment of mental health disorders. The insights thus gained may be turned into actions such as: identifying correlations between the contents of therapy interactions and (clinical) outcomes for the patient; making recommendations to the therapist (human or digital); and providing automated, unbiased assessment or measurement of the content or quality of therapy interactions.

FIGURES

Figure 4:
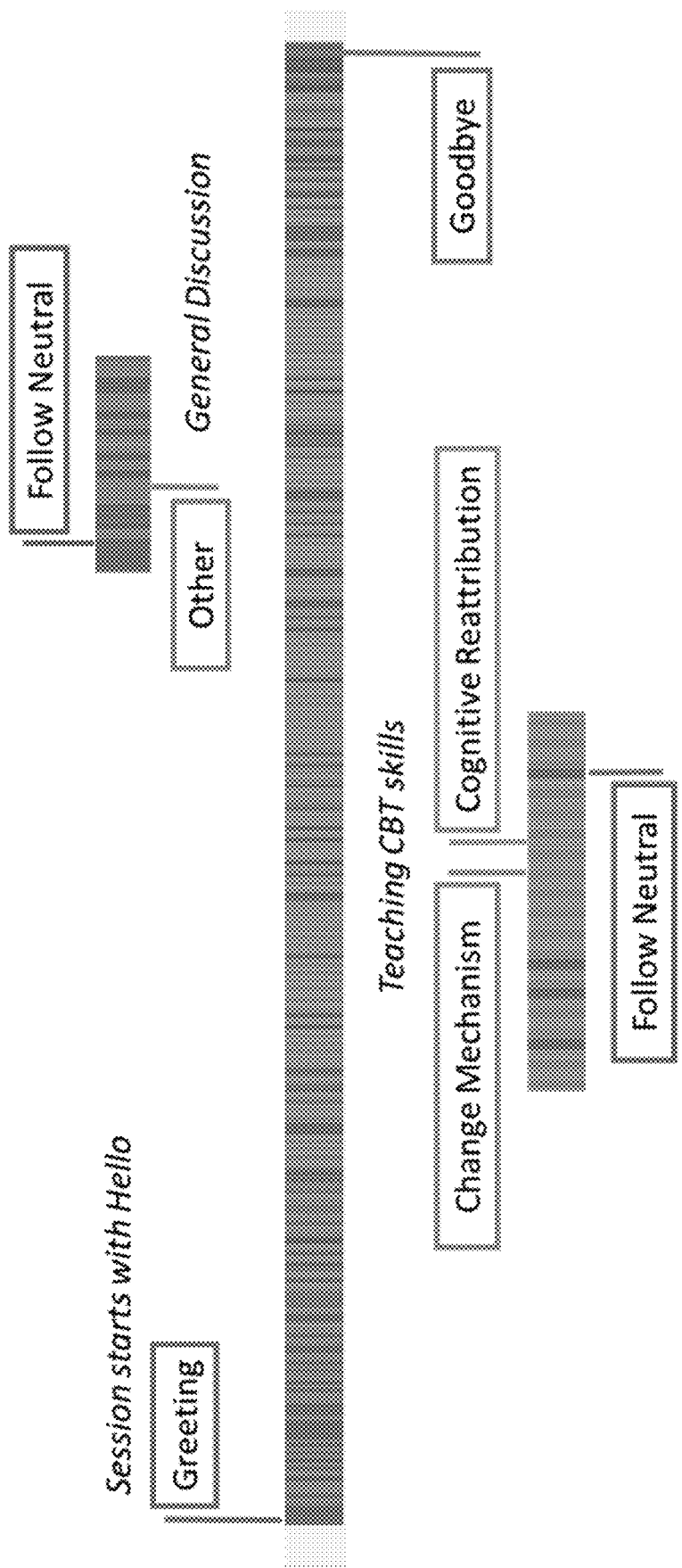

FIG. 4 is a graphical representation of a transcript of a therapy session segmented into utterances, each utterance having been classified as corresponding to one or more category (vertical bars, different shades of greyscale representing different categories). The start of the therapy session is on the left of the figure, the end of the session is on the right of the figure, thereby the chronological sequence of utterance categories that occurred during the therapy session is shown. Sections of the transcript have been magnified to demonstrate differences in utterance sequencing during the time course of the therapy session.

Figure 5:
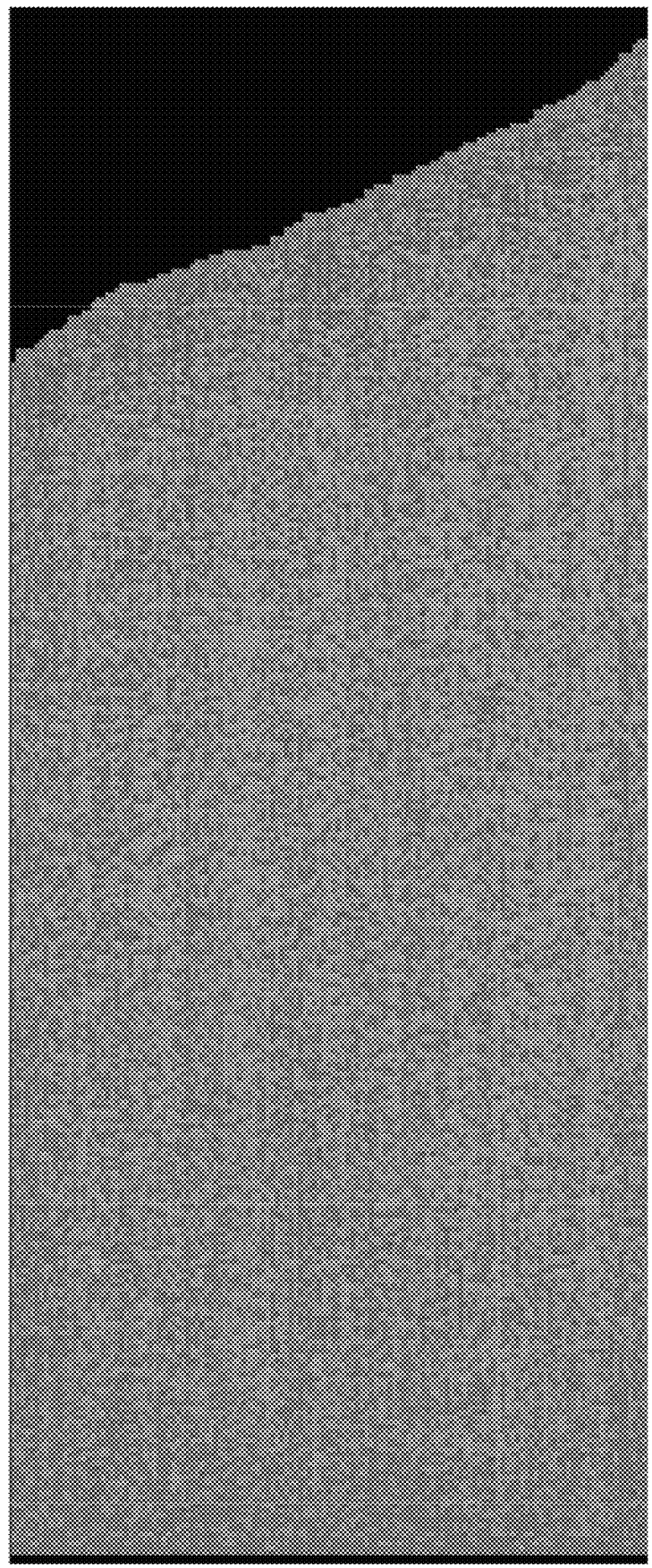

FIG. 5 is a stack of graphical representations of transcripts of therapy sessions such as that shown in FIG. 4, with time=0 for each graphical representation being aligned on the left of the figure. The variability between transcripts can be observed.

FIG. 6 is an alternative graphical representation (a punch card chart) of a transcript of a therapy session segmented into utterances, each utterance having been classified as corresponding to one or more category (vertical bars), wherein different categories of utterance are represented in different rows of the chart. The start of the therapy session is on the left of the figure, the end of the session is on the right of the figure, thereby the chronological sequence of categories that occurred during the therapy session is shown.

Figure 6A:
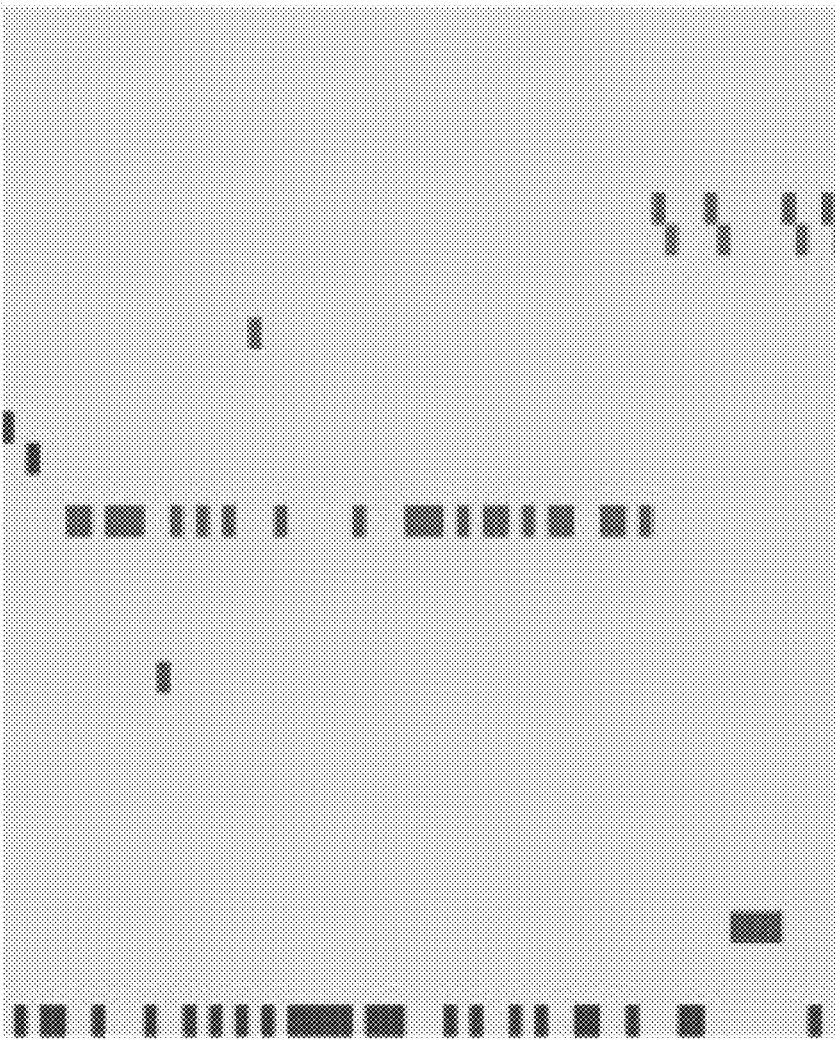
Figure 6B:
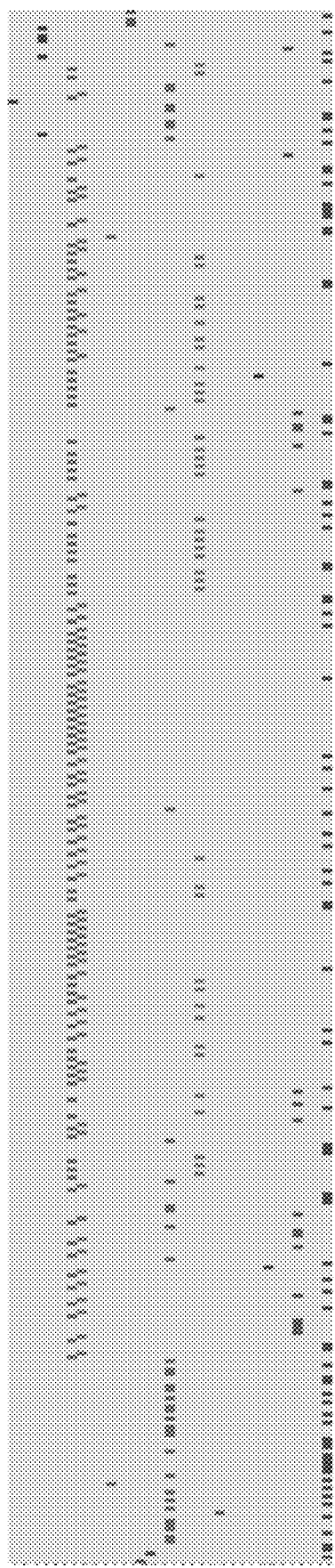

FIG. 6A is a magnified view of the start of the therapy session showing the different utterance categories, FIG. 6B shows an overall view of the whole therapy session. The exemplary utterance categories shown, in order from top to bottom of the figure, are the same as those in Table 1.

Figure 7:
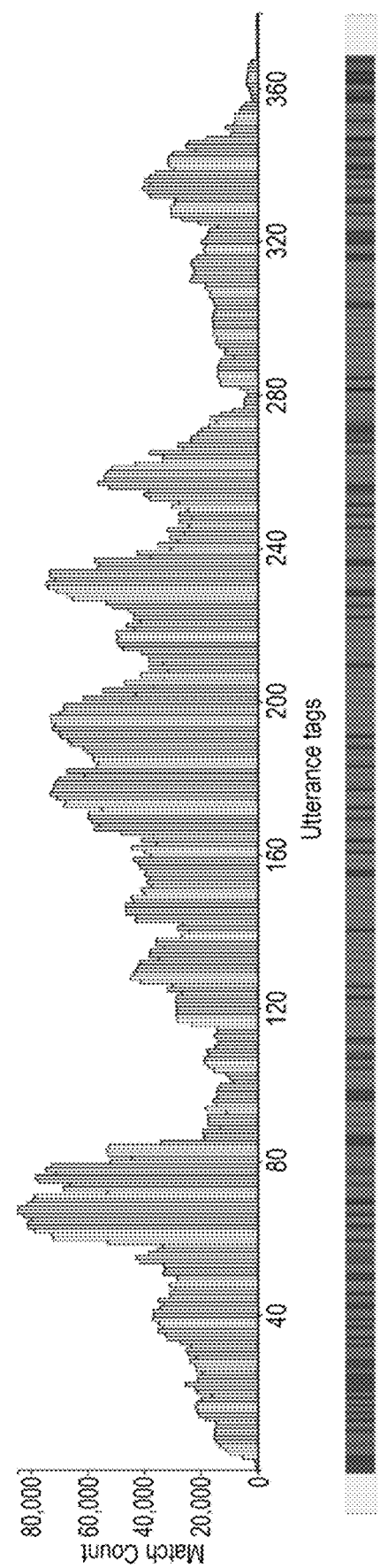

FIG. 7 is a bar chart showing match counts determined by a local sequence alignment algorithm for each utterance category present in a query transcript (represented below the bar chart in a graphical representation similar to that in FIG. 4), where the match counts are generated by a Smith Waterman algorithm that determines local regions of similarity (sub-sequences) between the query transcript utterance categories and a plurality of other transcripts. Here the plurality of other transcripts relate to over 200,000 hours of psychotherapy sessions. Each bar on the chart represents the match count for one individual utterance category, representing all transcripts that contain a sub-sequence containing that utterance category and meeting a threshold similarity criterion. Each transcript may be counted more than once if it contains more than one matching sub-sequence. Regions of the bar chart with higher match counts indicate regions of utterance category sub-sequence that are present in a greater proportion of the plurality of other transcripts than regions with lower match counts.

Figure 8:
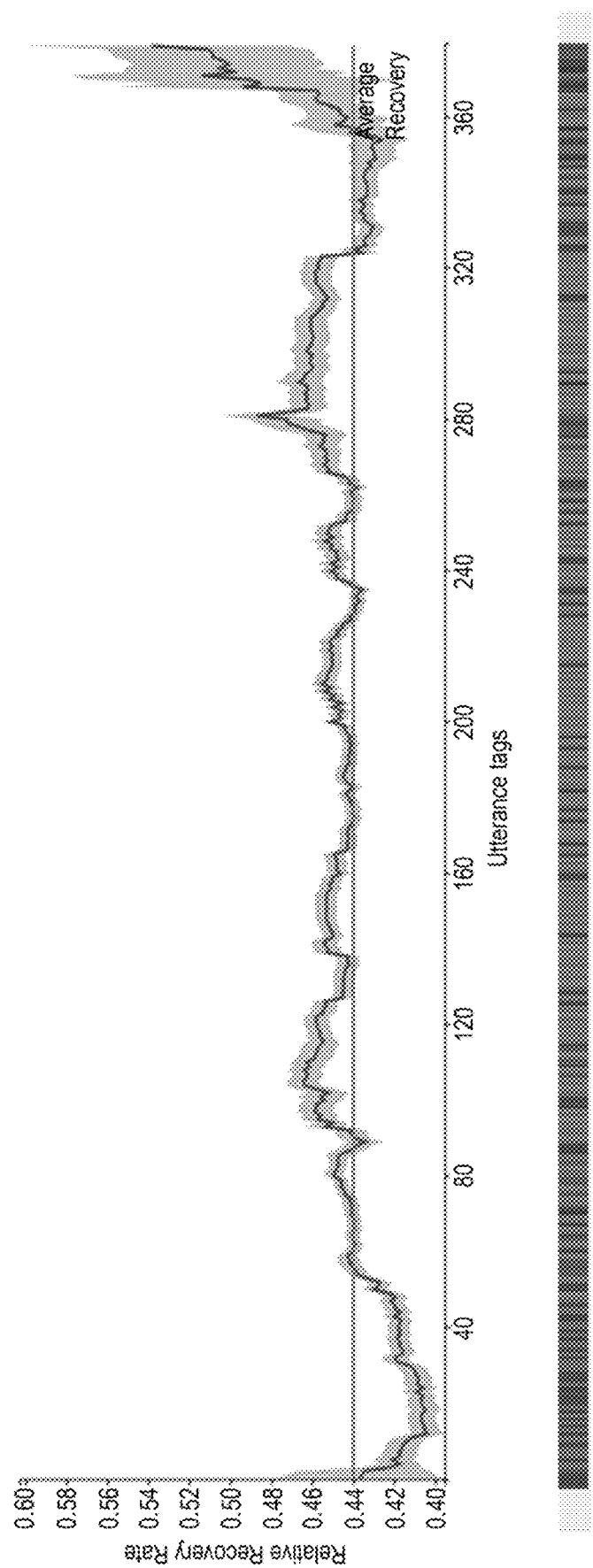

FIG. 8 is a graph showing the association between the presence of utterance category sub-sequences and clinical response to treatment. Utterance categories for a query transcript are shown in chronological order on the X-axis, correlated (predicted) recovery rate is shown on the Y-axis. Utterance categories in the query transcript were aligned against transcripts representing 200,000 hours of therapy using a modified version of the Smith Waterman Local Alignment algorithm in order to determine regions (sub-sequences) of local similarity; a recovery rate for each query transcript category sub-sequence was thereby determined by correlation with the mean of known recovery rates for all other transcripts that contained that sub-sequence. Each point on the line shows the recovery rate corresponding to one individual utterance category, representing the mean recovery rate for all transcripts that contain a sub-sequence containing that utterance category and meeting a threshold similarity criterion. A credible interval for each point is shown. Average recovery rate for all patients in the cohort is at 45.2%.

Figure 9:
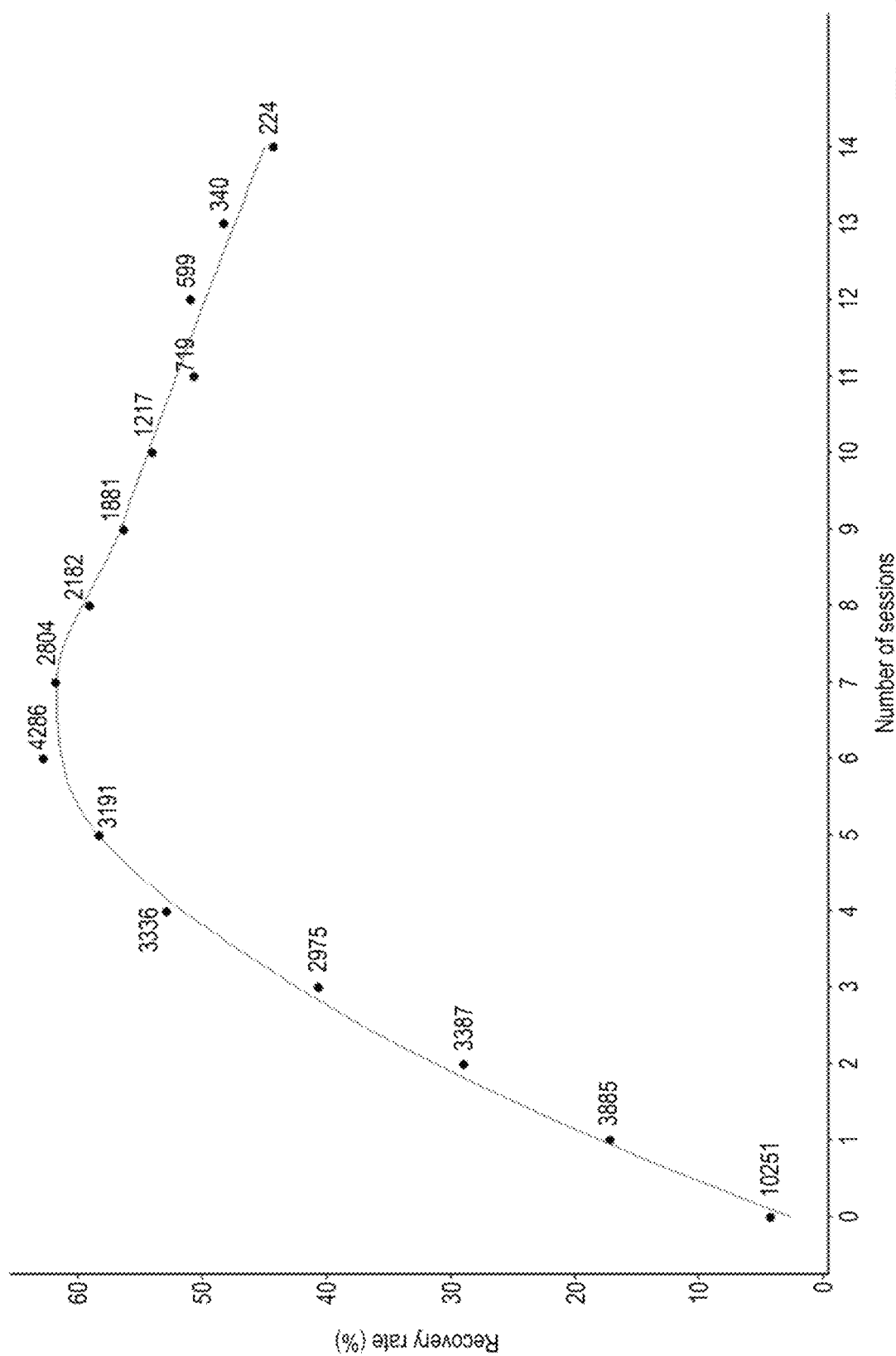

FIG. 9 is a graph showing a dose response profile for total psychotherapy sessions received by a patient. The total number of sessions of therapy delivered to individual patients is on the X-axis, and the corresponding recovery rate (%) for patients is shown on the Y-axis. The number of individual patients (n>200) receiving a particular number of sessions is shown next to each datapoint. The dose response profile shows that recovery rate increases up to approximately 6-7 sessions of therapy received; the recovery rate can be seen to reduce for patients where the number of sessions of therapy is greater than 7.

Figure 10:
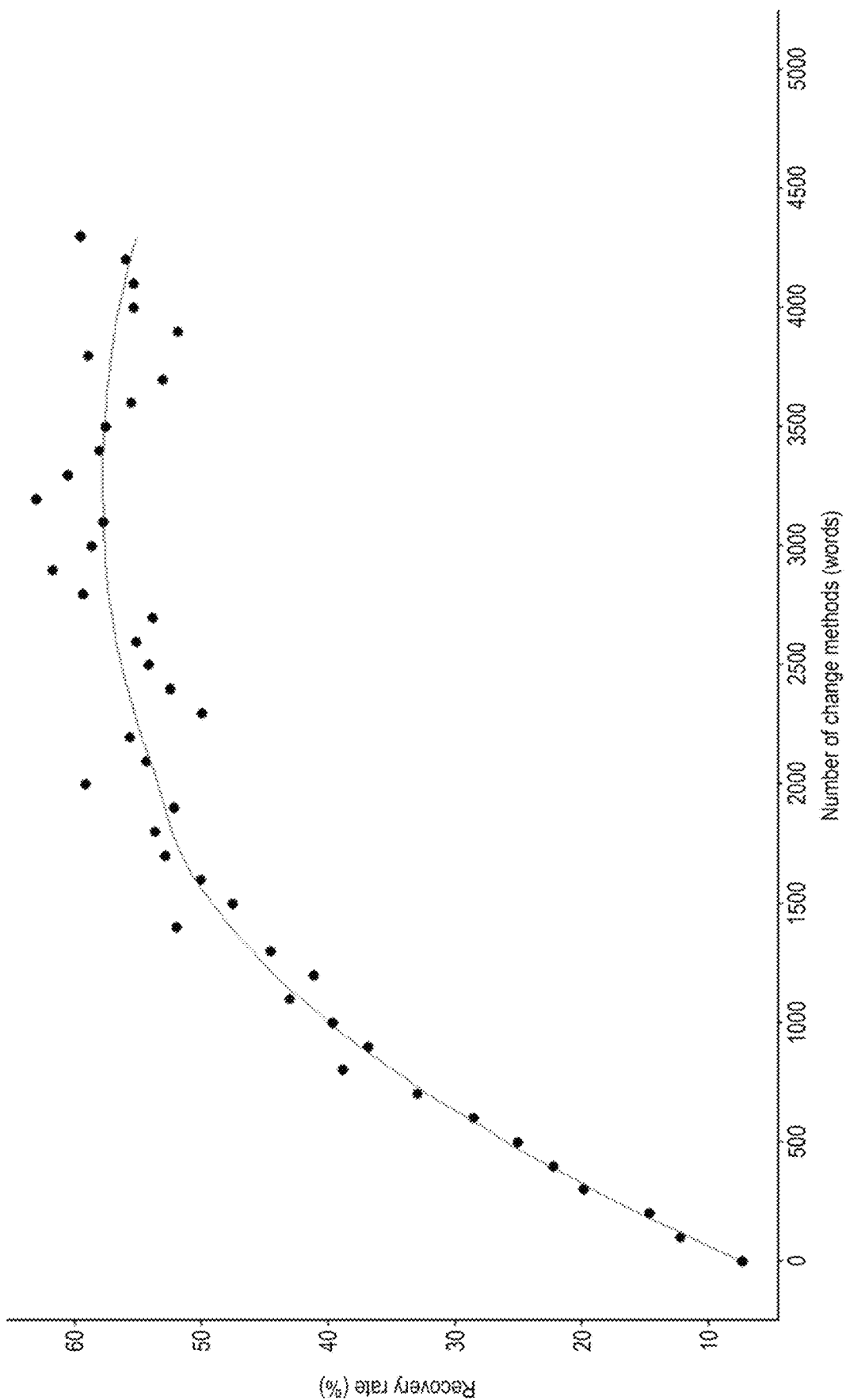

FIG. 10 is a graph showing a dose response profile for the dose of 'change mechanism' ('change methods') utterances received by a patient (i.e. delivered by a therapist) during the course of all therapy sessions for that patient. The total number of 'change mechanism' words delivered to individual patients is on the X-axis, and the corresponding recovery rate for those patients is shown on the Y-axis. The number of words is used as opposed to the number of utterances of that category in order to control for variable utterance length. Each datapoint represents the mean recovery rate of all patients (n>200) that received up to a particular number of 'change mechanism' words. It can be seen that recovery rate increases linearly up to about 1250 words of 'change mechanism' received; thereafter recovery rate increases more slowly with increasing dose of 'change mechanism' words until a plateau is reached at approximately 3000 words.

Interactions between two parties, such as written or spoken conversations or dialogue, are highly variable, both in terms of length (time-span) and content (number and type of utterance). Time-span is straightforward to determine, but the analysis of the content of interactions is more difficult, but also more important when assessing the quality of the interaction. A short, effective interaction may be of higher quality than a long interaction with a poorer outcome. Moreover, the ability to assess the content and quality of an interaction in an unbiased way permits feedback to be given regarding how to improve that or future interactions, thereby increasing quality of interactions over time.

One example of an interaction between two parties where the ability to assess the content and quality of the interaction is valuable is the interaction between a therapy agent and a client/patient, for example a patient seeking treatment for a mental health disorder. Compared to treatment of physical conditions, the quality of care of mental health disorders remains poor and the rate of improvement in treatment is slow (A. M. Kilbourne et al., Measuring and improving the quality of mental health care: a global perspective. *World Psychiatry*. 2018 February; 17(1):30-38). Outcomes for many mental disorders have stagnated since the original treatments were developed and in some cases the efficacy of psychotherapy appears to be reducing over time. One of the reasons for the gap in quality of care is the lack of systematic methods for measuring quality in the delivery of psychotherapy. As with any evidence based intervention, in order for treatment to be effective it needs to be delivered as intended (also known as treatment integrity). Improving the effectiveness of psychotherapy is therefore dependent upon accurate measurement of how treatment is delivered. However, while it is relatively simple to monitor the integrity and delivery of most medical treatments (e.g. the dosage of a prescribed drug), monitoring the delivery or 'dosage' of psychotherapy is a significantly greater challenge. Most psychotherapeutic treatments comprise a series of private discussions between the patient and clinician. Monitoring the delivery of this type of treatment to the same extent as physical medicine has previously required infrastructure and resources beyond the scope of most healthcare providers.

NICE (National Institute for Heath and Care Excellence) and the APA (American Psychological Association) currently recommend Cognitive Behavioural Therapy (CBT) as a treatment for most common mental health problems, such as depression and anxiety-related disorders. CBT refers to a class of psychotherapeutic interventions informed by the principle that mental disorders are maintained by cognitive and behavioural phenomena, and that modifying these maintaining factors helps produce enduring improvements in patient's presenting symptomology. One third of patients referred to the Improving Access to Psychological Therapies (IAPT) programme in the National Health Service in England in 2016/2017 received CBT, and CBT is among the most common treatment types offered to patients in the US. Despite its widespread use, IAPT currently includes no objective measure of treatment integrity for CBT, while only 3.5% of psychotherapy randomized controlled trials (RCTs) are reported to use adequate treatment integrity procedures.

CBT is the most researched form of psychotherapy and is described as an "evidence based" treatment, however the vast majority of "evidence" refers to gross measures of treatment outcomes; with relatively few studies investigating the mechanisms of treatment. Quantifiable measures of treatment delivered are needed not only to develop an understanding of the relationship between the 'dosage' of specific aspects of CBT and outcomes, but also, for example, for the development of new psychological treatments needed for the large number of people who do not respond to existing interventions.

Whilst the dose of a medication would easily be understood to be a function of e.g. its purity, the amount delivered and/or its biological availability, the dose of psychotherapy has previously been challenging to define or measure. The ability to measure the dose of psychotherapy delivered during one or more therapeutic interaction (e.g. therapy session) between a patient and a therapist by objectively measuring the content of the interaction provides a level of granularity that was not previously possible. By determining which therapy component(s) provided during a therapeutic interaction correlate with patient outcome, and optionally by determining which particular combination(s) or pattern(s) of therapy component correlate with patient outcome, the dose of psychotherapy delivered in subsequent therapy, where patient outcome is unknown, can be determined. Thereby various beneficial interventions can be provided in therapy delivered by a human therapist, such as increasing the dose of subsequent psychotherapy if appropriate, providing real-time or live therapist prompts to deliver improved therapy, providing further therapist training, re-allocating a patient to a different therapist etc. Where psychotherapy is provided by a non-human therapist, for example an autonomous mental healthcare technology such as a digital therapeutic or a digital therapy app, the dose of therapy can be automatically tailored to the patient's needs in real time by delivering the particular therapy component(s), or combination(s) or pattern(s) of therapy component known to correlate with improved patient outcome.

The CTSR (Cognitive Therapy Scale Revised (https://www.getselfhelp.co.uk/docs/CTSR.pdf)) tool is the current standard instrument for measuring the competency of CBT practitioners, and is used in both the UK and USA, for example. It is a manual tool whereby a (human) supervisor assesses the competency of a therapist by marking 12 quality items on a 0-6 scale according to how well the therapist displayed those quality items during a particular treatment session. Prior to the development of the CTSR, a previous version, the CTS, was used. Due to the way the CTSR assessment is carried out, and the consequent supervisor time necessitated by this, the assessment is usually only applied to a limited number of therapy sessions. Therefore therapist competency is not assessed for the vast majority of therapy sessions delivered. Furthermore, the quality of the measurement of therapist competency is itself dependent on the ability of the supervisor to use the CTSR scale (or other manual quality assessment measure) effectively. Therefore different supervisors may make divergent assessments of a particular therapy session/therapist competency using the existing manual assessment methods (i.e. inter-rater reliability may be low).

The traditional method of measuring the relationship between treatment delivered and outcomes is to use observational coding methods, typically involving the manual transcription of therapeutic conversations or post-session therapist self-assessment. These are resource intensive exercises which typically means that most studies focus on the effect of a small number of therapeutic factors in a relatively small sample of patients. To investigate the effect of specific therapeutic factors (or components), previous studies have typically added or removed a component of therapy (e.g. a particular type of therapist intervention) and measured the effect of this manipulation on outcomes. As with all RCTs, the results of these experimental interventions are difficult to transfer to 'real world' psychotherapy and to be meaningful would require sample sizes that are larger than those typically used. Furthermore, adding or removing a component of therapy delivered by the therapist is a blunt instrument, and does not take into account synergistic effects that may occur between different components of therapy and/or with the patient's response to those components, for example depending on different components' proximity to each other within the therapy interaction/session.

Improved methods of quantifying treatment delivered (therapy dose) must therefore be able to simultaneously measure multiple factors of a therapy session and their relationship to each other, be applied in a natural clinical context, and be gathered from a sufficiently large enough sample to draw meaningful conclusions. Furthermore, the ability to assess the relationship and interaction between different parts of a therapy session, or different types of therapeutic intervention/therapy components and the timing of their delivery relative to each other, permits more accurate conclusions to be drawn about the most effective delivery of therapy.

In internet-enabled CBT (IECBT), a patient communicates with a qualified CBT therapist using a real-time text based message system. IECBT has been shown to be clinically effective for the treatment of depression and is currently deployed within IAPT. Another advantage of IECBT is it permits the collection of large amounts of data describing therapy i.e. transcripts of therapy sessions (interactions) between therapists (agents) and patients (clients), and also outcome data associated with the transcripts. These transcripts can therefore be used to develop methods for the accurate, unbiased assessment of transcript data; the methods are applicable to the analysis of therapy, but are also expected to be applicable to transcript data from other domains e.g. education or sales.

The transcripts can be divided into individual utterances made by either party e.g. a therapist (agent) or a patient (client). Using a deep learning approach, a model was developed to automatically categorise (assign a semantic representation to) therapist (agent) and patient (client) utterances gathered during therapy. In order to train the model, human annotations were first applied to a subset of therapy transcripts. The trained model was then applied to a large-scale transcript dataset (representing more than 200,000 hours of therapy) to assign one or more categories to all utterances. Each therapy transcript could therefore be represented as a sequence of utterance categories. Outcome data (e.g. patient recovery, patient improvement, patient engagement) was also available for all transcripts in the dataset. A fuzzy sequence matching algorithm (e.g. a local sequence alignment algorithm) was then used to determine regions of matching (similar) sequence between a query sequence (representing a query transcript) and (a sub-set of) the large-scale transcript dataset. Thereby, information about the likely outcome of the query sequence (transcript) could be provided, by correlation with the known outcomes of (the sub-set of) the large-scale transcript dataset with which matching sequence regions were shared. Furthermore, information about the most effective regions of the sequence (and therefore transcript) was provided by the method.

The present approach therefore provides methods and systems for assessment of transcript data, in order to determine likely outcome arising from the data, leading to the potential for systematic improvement and quality control of the interactions from which the transcript data derives, for example mental health treatment.

Computer-Based System (Computer-Implemented System, Device or Apparatus)

A computer-based system for facilitating an interaction between two parties, for example a therapy agent and a patient (client) undertaking therapy, and/or for analysing transcript data derived from that interaction, includes a plurality of devices connectable to a server via a network system.

The system preferably enables e.g. therapists and patients to use devices to interact using text-based messages and/or spoken conversation (speech data) during sessions of interaction (e.g. therapy), or for an analyst to obtain transcript data relating to those interactions and analyse that data.

Each device may be a mobile device, such as a laptop, tablet, smartphone, wearable device, etc. Each device may be a (nominally) non-mobile device, such as desktop computer, etc. Each device may be of any suitable type, such as a ubiquitous computing device, etc.

A (typical) device includes one or more processor(s), memory, storage, one or more network interfaces(s), and one or more user interface (UI) device(s). The one or more processors communicate with other elements of the device via one or more buses, either directly or via one or more interfaces. The memory includes volatile memory such as dynamic random-access memory. Among other things, the volatile memory is used by the one or more processors for temporary data storage, e.g. when controlling the operation of other elements of the device or when moving data between elements of the device. The memory includes non-volatile memory such as flash memory. Among other things, the non-volatile memory may store a basic input/output system (BIOS). The storage includes e.g. solid-state storage and/or one or more hard disk drives. The storage stores computer-readable instructions (SW). The computer-readable instructions include system software and application software. The application software may include a web browser software application (hereinafter referred to simply as a web browser) among other things. The storage also stores data for use by the device. The one or more network interfaces communicate with one or more types of network, for example an Ethernet network, a wireless local area network, a mobile/cellular data network, etc. The one or more user interface devices may include a display and other output devices such as loudspeakers. The one or more user interface devices may include a keyboard, pointing device (e.g. mouse) and/or a touchscreen, and other input device such as microphones, sensors, etc. Hence the device is able to provide a user interface for e.g. a patient or therapist or analyst.

A (typical) server may include one or more processors, memory, storage, one or more network interfaces, and one or more buses. The elements of the server are similar to the corresponding elements of the device. The storage stores computer-readable instructions (SW) (including system software and application software) and data associated with the server. The application software may include a web server among other things. Alternatively/additionally, the server may correspond to a virtual machine, a part of a cloud computing system, a computer cluster, etc., for example a 'serverless' supercomputer.

The network system may include a plurality of networks, including one or more local area networks (e.g. Ethernet networks, Wi-Fi networks), one or more mobile/cellular data networks (e.g. $2^{nd}$, $3^{nd}$, $4^{th}$ generation networks) and the Internet. Each device is connectable to the server via at least a part of the network system. Hence each device is able to send and receive data (e.g. data constituting speech) to and from the server.

Method

Figure 1:
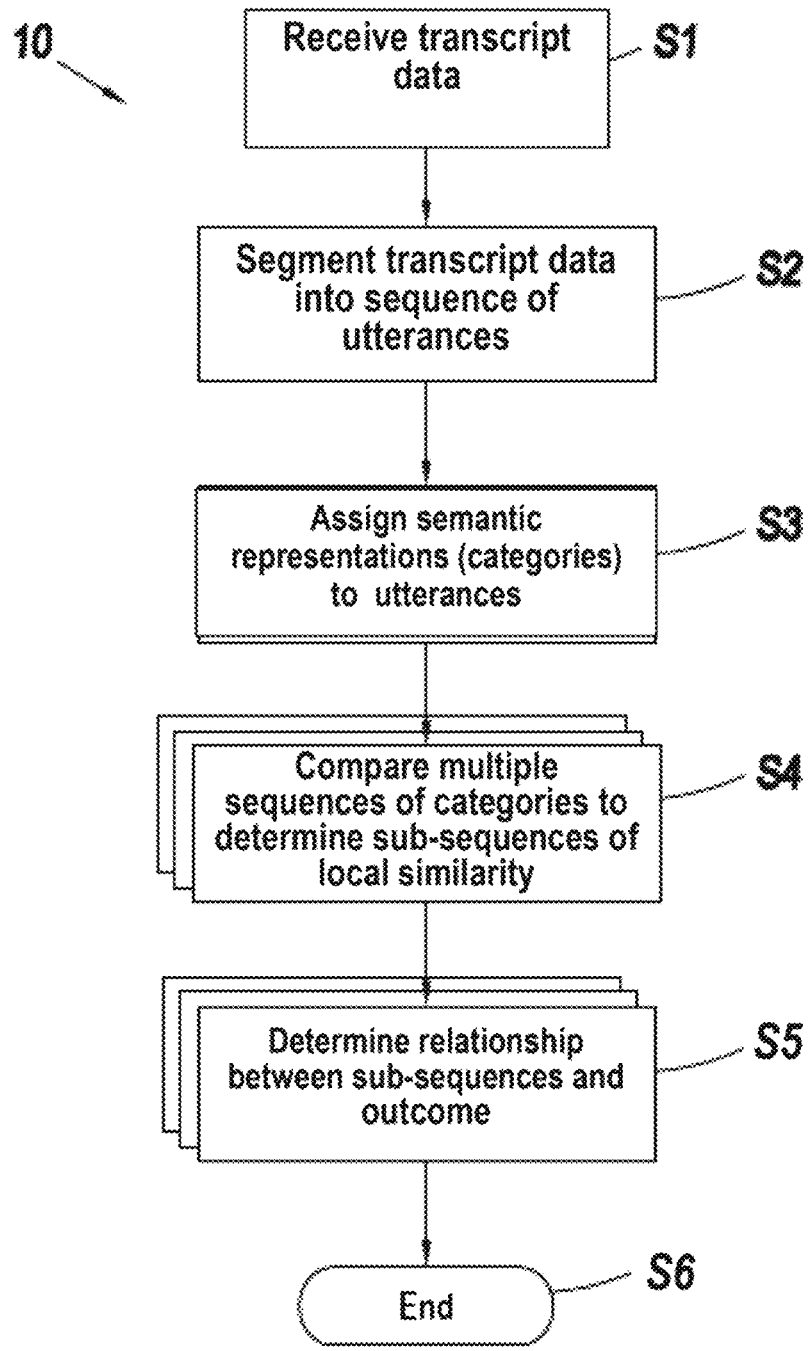
FIG. 1 illustrates the method of the invention.

Referring to FIG. 1, the system may perform a method 10 comprising several steps S1-S6.

Steps S1 to S3 are also described in international application PCT/GB2019/051380 (which is hereby incorporated by reference).

Training (Model Development) and Prediction Phases

The third step S3 (assigning semantic representation(s) to utterances) involves a deep learning model. Such a model typically has model inputs, model parameters and model outputs.

Training data (hereinafter referred to as a training dataset) is used during the training phase for the model. In some examples, the training dataset includes multiple instances of e.g. human-assigned data. During the training phase, the instances of data are provided as model inputs, and the model parameters are adjusted (i.e. the model is constructed) such that the model outputs optimally predict (assign) the corresponding semantic representations (e.g. labels, tags). All of the data in the training dataset is used collectively to construct the model.

During the prediction phase, an instance of unassigned (e.g. unlabelled, untagged, unclassified) transcript data is inputted to the first part of the constructed model which outputs a corresponding prediction of the semantic representations (e.g. labels, tags, categories, classifications). These (assigned utterances) are then formed (aggregated) into a representation of the therapy session (a sequence of categories), which is then compared with other sequences using a fuzzy sequence matching algorithm.

First Step of the Method

Figure 2:
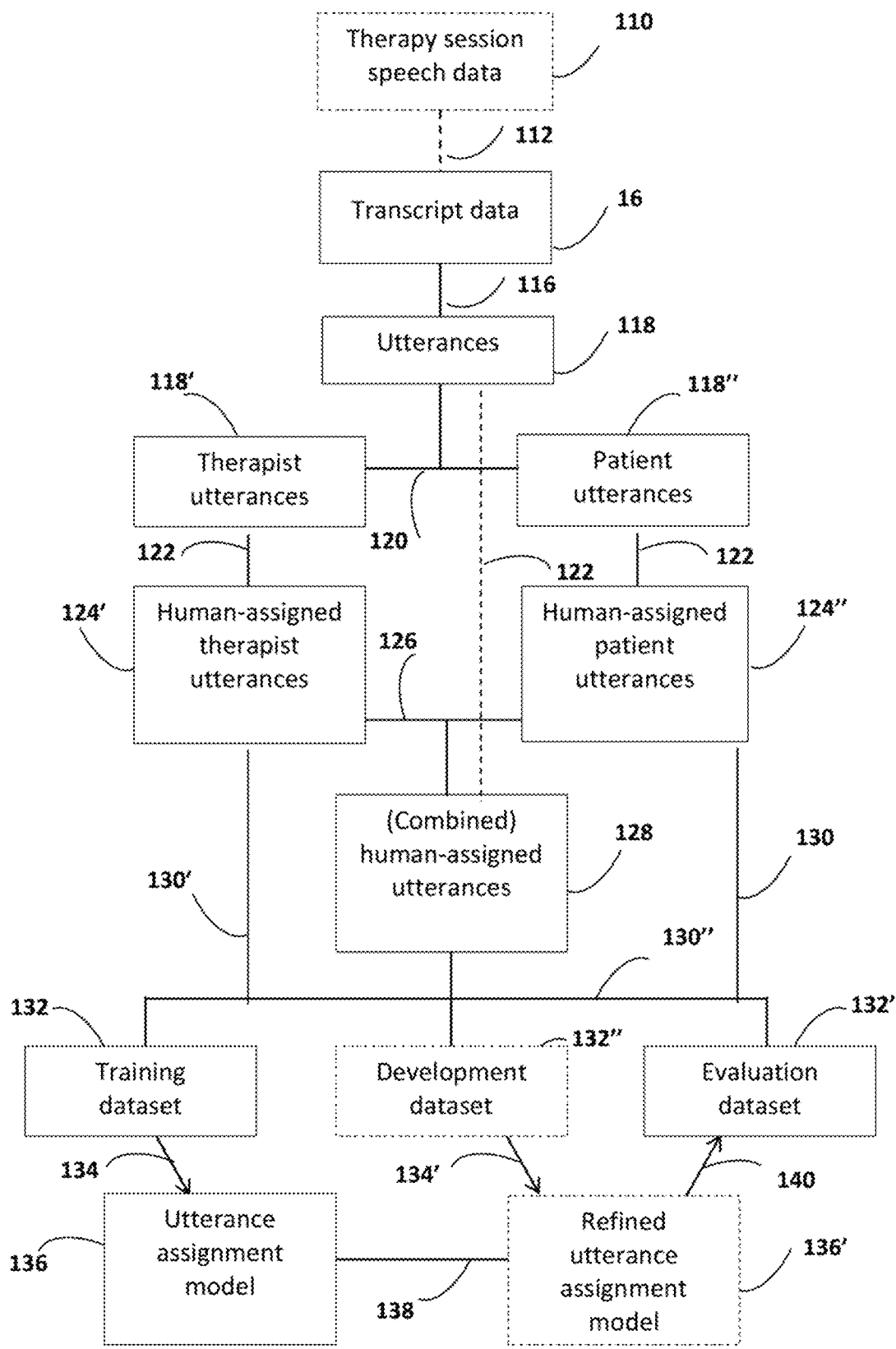
FIG. 2 illustrates an exemplary development method of an utterance assignment model which may be used in a method of the invention.
Figure 3:
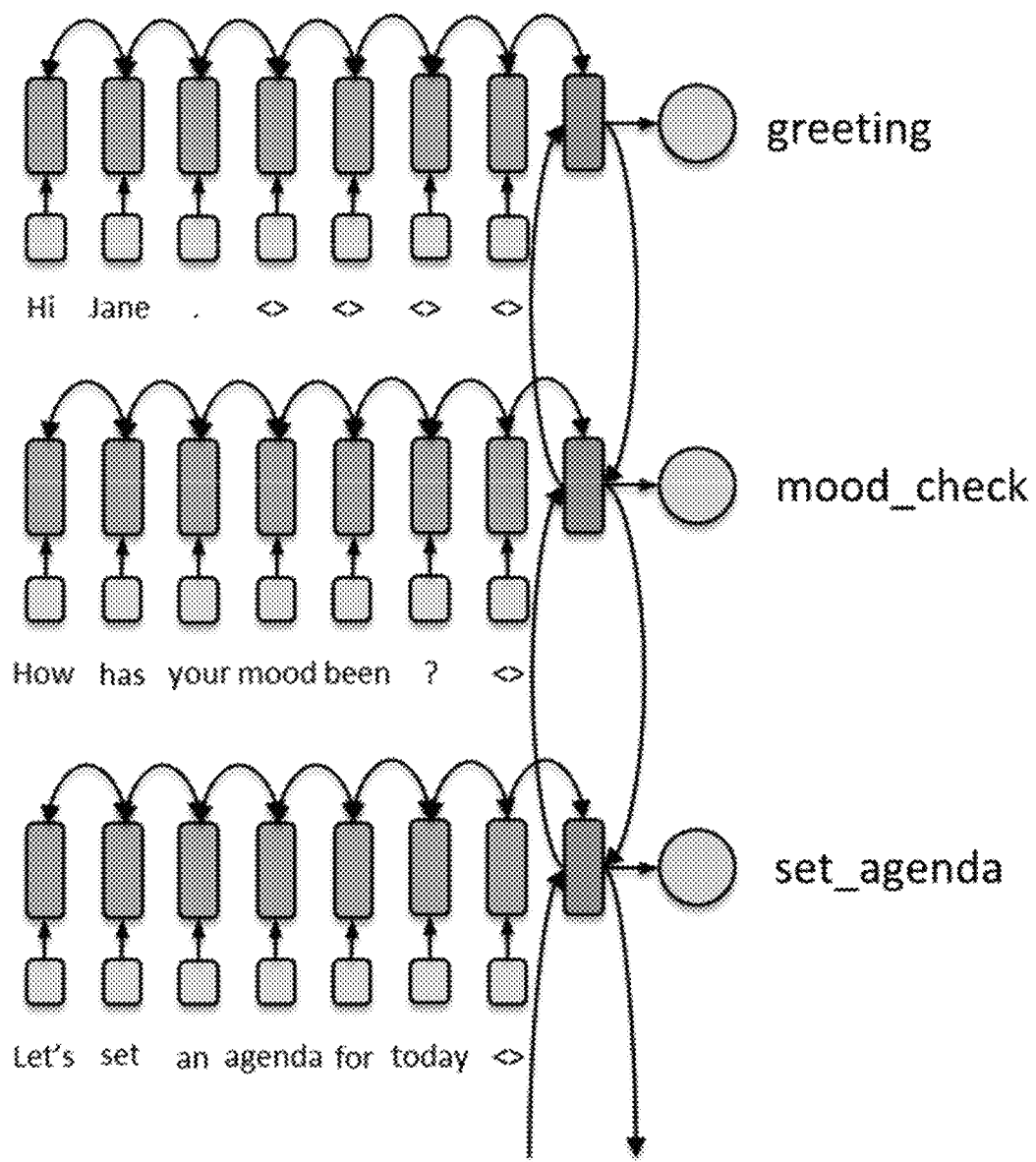
FIG. 3 is a high-level illustration of an utterance assignment model architecture, when tagging is used to assign meaning to utterances (classify each utterance as corresponding to one or more categories; tagging each utterance).

Referring in particular to exemplary FIGS. 1, 2 and 3, at a first step S1, transcript data 16 is received. The transcript data 16 relates to one or more interaction. A therapy session is an example of an interaction. The transcript data 16 may be referred to as therapy session transcript(s). The one or more interaction (e.g. therapy session) may be of any length. The transcript data 16 is provided by e.g. the patient and/or by the therapist. The transcript data relates to e.g. the patient and/or the therapist. The transcript may include free(form) text, i.e. any text may be provided by e.g. the patient or the therapist. The transcript may be in English or in any other language. Where the transcript relates to a therapy session, it may be any type of therapy session, for example a psychotherapy session, a talking therapy session, or a coaching session.

The transcript data 16 may be obtained (received) in any suitable way. For example, the transcript may be inputted as (typed) text by the patient and/or the therapist using a patient interface or a therapist interface of a system, device or apparatus. Optionally, other methods of transcript data input may be used such as any standard ASR (Automatic Speech Recognition) system to convert 112 the sounds of speech (e.g. therapy session speech data 110) into words (transcript data 16). The transcript data 16 need not be provided directly by e.g. the patient or the therapist.

Second Step of the Method

At a second step S2 the transcript data 16 is segmented (divided) 116 into a sequence of utterances 118. The utterances represent short passages/phrases/sentences of speech (conversation, communication). The transcript data may be divided into utterances at source i.e. when a therapist and a patient exchange text-based messages each individual message in the exchange is considered one utterance. If ASR is used to convert speech into words (text data) the ASR system may nominate portions of speech (e.g. divided by pauses) as individual utterances. Alternatively if a contiguous transcript of an interaction (e.g therapy session) is provided, this may be subsequently divided into individual utterances.

The utterances 118 from an (exemplary) therapy session may be segmented 120 into therapist utterances 118' and patient utterances 118". Each utterance may be automatically identified at source as deriving from either the patient or the therapist by tagging with the particular user interface from which it originated (patient interface or therapist interface). Alternatively, each utterance may subsequently be identified as deriving from either the patient or the therapist. Either the patient utterances 118", the therapist utterances 118' (or a combination of both patient utterances and therapist utterances) may be analysed.

Alternatively, where a contiguous transcript (text data) of a therapy session is provided it may not be possible to identify the source of each utterance as deriving from either the patient or the therapist, in which case the invention may be performed on/with the totality of the transcript data.

Information relating to the relationship between individual utterances (the order of the utterances during the therapy session) is retained along with the utterance and used in the methods and systems of the invention; this provides a richer source of information for use in assigning meaning to the utterances, and results in the segmentation of the transcript into a (chronological) sequence of utterances.

During a therapy session, the therapist and patient interact. The therapist poses questions or makes statements (together considered therapist utterances 118'), to which the patient then responds with patient utterances 118". Examples of therapist (agent) utterances and patient (client) utterances are included below.

Steps S1 and S2 of the method may be considered as separate steps, or suitably they may be considered as one combined step, such that the transcript data when received is already segmented into a sequence of utterances.

The method may also involve obtaining further data relating to the patient (this further data may be referred to as patient data). The patient data may include data relating to patient variables, for example personal data such as age, gender, etc., medical data such as medication use, drugs/alcohol misuse, etc., and so forth. The patient data may be provided by the patient using a patient interface or may be obtained in any other suitable way. The further data relating to the patient may be retained with the transcript data or sequence of utterances in order that a relationship may optionally be determined between the further data, and/or the transcript data, and/or the sequence of utterances.

Third Step of the Method

At a third step S3, semantic representations are assigned to the utterances, such that each utterance is classified as corresponding to one or more categories from a predetermined list of categories. This involves using deep learning processes which may be referred to as a (deep learning) utterance assignment model 136, or a (deep learning) therapy insights model.

One or more semantic representations (meanings, categories) may be assigned to the utterances by the model 136 in a number of ways including:
- Identification of intent of an utterance
- Identification of intent of an utterance and identification of slots
- Embedding in a semantic space
- Classifying (tagging) utterances Therefore (assigned) utterances are those to which one or more meaning (category) has been assigned by any suitable method. Each utterance may be tagged with the one or more category such that the transcript can be read as a sequence of categories.

For example, a first part of a deep learning model may assign a semantic representation that encodes meaning to each of the plurality of utterances in context.

One such semantic representation is a distributed semantic representation which often consists of a fixed-size dense vector that can be used as input to other systems that can provide semantics on a more specific level (such as classification, sentiment analysis, and/or intent representation). The method may use these distributed semantic representations as input to a classification system which assigns one or more tags to an utterance. These tags convey the role that the utterance plays in therapy. However, more broadly these distributed semantic representations can also be used as input to a system to determine the sentiment of the utterance (e.g. positive, neutral, negative). Furthermore, the distributed semantic representations can be used as input to a system that translates the utterance into an intent representation. An intent representation encapsulates an action or goal that the speaker wishes to achieve and can be associated with optional or required parameters.

The development of the utterance assignment model may be understood by reference to FIGS. 2 and 3. Referring in particular to FIG. 2 which illustrates an exemplary development (learning, training) phase of a utterance assignment model, following the division 116 of the transcript data 16 into utterances 118, which optionally may further be divided 120 into therapist utterances 118' and/or patient utterances 118", the utterances are manually-assigned (with a semantic representation) 122 to produce human-assigned utterances. The human assigned utterances may comprise human-assigned therapist utterances 124', or human-assigned patient utterances 124", or combined human-assigned utterances 128. Combined human-assigned utterances 128 may be produced by manually-assigning 122 the (original, undivided) utterances 118, or by combining 126 the human-assigned therapist utterances 124' and the human-assigned patient utterances 124".

For example, human-assigned utterances may be produced by manually allocating each utterance to one of a plurality of suitably designed tags (categories). Examples of suitable tags and their design rationale may be found below. The suitability of the tags will be determined by the particular characteristics of the input data, and may be determined empirically.

Following manual assignment to semantic representations 122, the human-assigned utterances 124',124",128 are divided 130',130" to one of a training dataset 132, an evaluation dataset 132' or optionally a development dataset 132". The training dataset 132 may be used to train 134 a deep learning utterance assignment model (this may also be referred to as the therapy insights model (TIM)). Following training 134 of the utterance assignment model 136 using the training dataset 132, the utterance assignment model 136 may optionally be further refined 138 by performing fine-tuning of training hyper parameters 134' using the development dataset 132". The performance of the utterance assignment model 136 or the refined utterance assignment model 136' may be evaluated using the evaluation dataset 132', which the utterance assignment model had not previously encountered.

If after training and/or evaluation the particular utterance semantic representations (e.g. categories, tags) designed do not appear to provide appropriate granularity of information relating to the therapy session transcripts (e.g. too many utterances are allocated to one or more semantic representations), the semantic representations used may be refined by the inclusion of one or more level of sub-representation. The model may thus be retrained using these one or more levels of sub-representations, in order to provide more detailed information relating to the transcripts/utterances.

Optionally, the utterance assignment model 136,136' may use active learning to identify transcripts that it finds difficult to assign meanings to (i.e. where the model finds it difficult to assign a plurality of utterances to one or more semantic representations with a high degree of certainty). These transcripts may be automatically recommended by the model for manual assignment. Such manually-assigned transcripts may be used to refine 138 the semantic representation assignment performance of the model 136,136'. Alternatively, the new manually-assigned transcripts may be added to the training dataset 132, and the training 134 of the utterance assignment model 136 may be re-run.

In one non-limiting example of the development of an utterance assignment model, following the division 116 of the text data 16 into utterances 118, which optionally may further be divided 120 into therapist utterances 118' and/or patient utterances 118", the utterances are assigned by human/manual annotation with tags ('tagged') 122 to produce human-annotated utterances. The human-annotated utterances may comprise human-annotated therapist utterances 124', or human-annotated patient utterances 124", or combined human-annotated utterances 128. Combined human-annotated utterances 128 may be produced by manually-annotating ('tagging') 122 the (original, undivided) utterances 118, or by combining 126 the human-annotated therapist utterances 124' and the human-annotated patient utterances 124".

In this example, the human-annotated (tagged) utterances are produced by manually allocating each utterance to one of a plurality of suitably designed tags (categories). Examples of suitable tags for both therapist and patient utterances and their design rationale may be found below. The suitability of the tags will be determined by the particular characteristics of the input data, and may be determined empirically.

Assigning a semantic representation to the utterances (classifying the utterances into categories) involves using the first part or portion of a deep learning model. The first part of the deep learning model may include a single layer or multiple stacked layers. The layers may be of various types, such as convolutional neural network layers (see Y. LeCun, L. Bottou, Y. Bengio and P. Haffner, "Gradient-based learning applied to document recognition," Proceedings of the IEEE, vol. 86, no. 11, p. 2278, 1998), recursive or recurrent neural network layers, long short-term memory layers (see S. Hochreiter and J. Schmidhuber, "Long short-term memory," Neural computation, vol. 9, no. 8, p. 1735, 1997), fully connected neural network layers, drop-out layers, and various nonlinearities such as sigmoid, tanh, ReLU, etc.

A deep neural network (DNN) refers to an artificial neural network endowed with complex structure. A convolutional neural network (CNN) is a type of DNN developed for object recognition in images. Recent research suggests that CNNs can also be applied to text, where they can spot linguistic indicators. CNNs ignore most text structure and are only sensitive to very local dependencies. A recurrent neural network (RNN) is a type of DNN that is sensitive to text structure. RNNs are particularly effective at encoding the semantics of short- and medium-length text snippets (up to a sentence). RNNs do not currently work very well on whole documents, although recent developments (e.g. RNNs with attention) attempt to address this issue. Hierarchical applications of RNNs are another way of addressing this shortcoming. One possible type of hierarchical RNN application is where one RNN focuses on the words in an utterance, while another one uses whole utterance representations as inputs.

The deep learning model may be a bidirectional long short-term memory (BiLSTM) neural network; this type of network may be beneficial when the relationship between individual words within an utterance is important for its classification. More specifically, the model may be a hierarchical bidirectional long short-term memory (HiBiLSTM) neural network. When assigning a meaning to (classifying) a particular utterance, the HiBiLSTM model has access to the information from all utterances in the transcript in the correct positions. This allows information from the utterance itself and from surrounding utterances to be used by the machine learning model. By incorporating hierarchical relationship data it is possible to assign meaning to (classify) an utterance by taking into account the content of the utterance and also the context of other neighbouring utterances (e.g. a 'mood_check' utterance tends to occur after a 'greetings' utterance. The use of a model capable of synthesizing a combination of multiple types of data leads to better assignment (e.g. classification and prediction by the model. FIG. 3 illustrates an exemplary HiBiLSTM model architecture.

Where suitable, another possibility is to use an utterance assignment model that does not use deep neural networks, employing instead simpler machine learning methods such as SVM (Support Vector Machines), logistic regression, decision trees, or other more complex techniques, such as random forests, or Bayesian graphical models.

Once the utterance assignment model 136,136' has been trained 134,134' with the manually (human)-assigned (e.g. tagged) data (the training dataset 132 and optionally the development dataset 132"), it may be used to assign semantic representations to the utterances present in additional (previously unseen) transcripts.

Assignment of semantic representations to utterances by the trained model may be more consistent than that achieved manually by human assignors (annotators). This is because there may be noise among human assignors (i.e. two humans will not agree 100% of the time on the task). The model is also capable of assigning utterances at a much faster rate than that achievable by human assignors. For example, when assigning semantic representations to utterances by tagging with one or more categories, experienced human annotators may be able to classify around 11,000 utterances (equivalent to ~290 hours of therapy session text data) in 200-500 person-hours, whereas the utterance assignment model (an utterance classification model in this case) can classify approximately 4 million utterances (equivalent to 100,000 hours of therapy) in about 45 minutes.

The representation of a therapy session (sequence of categories relating to the utterances in chronological order) may be outputted by the model in real-time (live) whilst a therapy session is ongoing, or ex post facto after the session has ended. It should be noted that as one or more categories can be assigned to a single utterance, by the deep-learning model or otherwise, the output of step S3 may comprise a chronologically ordered sequence of categories having a number of components that is greater than the number of segmented utterances contained in the input transcript data.

Fourth Step of the Method

Referring again to FIG. 1, at a fourth step S4, the sequence of categories representing a transcript is compared with sequences of categories representing a plurality of other transcripts using a fuzzy sequence matching algorithm, the plurality of other transcripts each having associated outcome data associating them with one or more outcomes.

The Smith Waterman Algorithm (Smith and Waterman, 1981, 'Identification of Common Molecular Subsequences', J Mol Biol, 147, 195-197) is an example of a fuzzy sequence matching algorithm. It is a local sequence alignment algorithm, meaning it finds matching subsequences regardless of their position in the sequences being compared, rather than the commonalities of a pair of whole sequences. It is commonly used for analyzing local similarities (homologies) between nucleic acid or amino acid sequences, and is the general and complete case of a number of heuristic optimisations such as BLAST (Basic Local Alignment Search Tool).

A group of therapy session transcripts may be pooled in order to provide the plurality of transcripts, for example those deriving from a particular patient, a particular patient group, a particular therapist or a particular therapist group may be pooled. Analysing data for a particular group may provide group-specific relationships. By selecting a dataset that relates to a particular group of therapy sessions (e.g. relating to a particular patient cohort), relationships specific to that group may be established.

The fuzzy sequence matching algorithm, such as the Smith Waterman Algorithm, is used to find one or more regions (sub-sequences) of the utterance sequence relating to (representing) the query transcript that match similar sub-sequences in the utterance sequences relating to (representing) the plurality of transcripts. The parameters that determine whether a region of the utterance sequence matches one or more of the sequences derived from the plurality of transcripts may be determined in any suitable way.

For example, when using a version of the Smith-Waterman algorithm to find matching sub-sequences between two whole sequences, a scoring matrix is generated for the two whole sequences which enables a sequence match score to be determined between any number of local subsequence regions within the two sequences.

The typical implementation of Smith-Waterman only finds the last match. We want all matches over a given cutoff. If this change is not made then it is not possible to fairly compare the beginning of a transcript with the end. As such, the algorithm was altered to allow multiple matches within the query sequence only. This means that the same matching region (for instance, teaching cognitive reattribution, can be used more than once in a single query). Further the algorithm then masks out the found region, recalculates the scoring matrix and then looks for additional matches.

There are a few variables which can be set/weighted in order to fine tune the behaviour of the algorithm:
- Match score: The reward for a tag matching in the two sequences at that pair of sites
- Mismatch cost: The penalty for not matching at that site
- Gap cost/extension cost: The penalty for allowing a tag on one sequence but ignoring the other.

These three parameters are enough to generate the scoring matrix where each site is the maximum score achievable given the preceding sequence of the two sequences where the score cannot fall below zero at any point. Furthermore, the results of the scoring matrix can be refined by defining a score cutoff, which is the maximal score achieved by the subsequence match. If the maximum score in the matrix is below the cut-off, it is not considered and the algorithm terminates.

A set of example parameters which were used in experiments according to the present invention were: Match score (3), Mismatch cost (5), Gap cost (5), Score cutoff (20).

Finding the optimal values for these variables is a process of trial and error which can vary according to the specific purposes for which the analysis is being carried out. Different numbers were trialled across several runs and a set of values was chosen based on whether legible and actionable differences in recovery rate in the graphs could be determined. Machine learning methods could be applied to optimize for a measurable outcome such as information theoretic content or variance of recovery rate in the graph.

Although the examples described herein relate to versions of the Smith-Waterman algorithm as the fuzzy sequence matching algorithm, it is envisioned that other fuzzy sequence matching algorithms are also suitable for use with the methods and systems provided by the present invention. Examples of alternative algorithms which would be suitable include the previously mentioned BLAST algorithm as well as models such as Hidden Markov Models (HMMs).

Thus the therapy insights deep learning model and the fuzzy sequence matching algorithm may be used in combination to analyse the transcript of a therapy session (a query transcript), to generate a sequence of categories relating to the whole transcript, and to match one or more sub-sequence(s) relating to regions showing above-threshold similarity (homology) with a subset comprising one or more of a plurality of other transcripts.

Fifth Step of the Method

Referring in particular to FIG. 1, at a fifth step S5, a relationship is determined between each of the one or more sub-sequences from step S4, and one or more outcomes based on the outcome data associated with the subset of transcripts which were determined, in step S4, to contain one or more sub-sequences of categories meeting the similarity threshold.

Determining the relationship often comprises determining a strength of correlation or anti-correlation between each sub-sequence of categories from the query transcript and each of the one or more outcomes in the outcome data for a matched subset.

Such relationship data can be further complemented by assigning a confidence interval or a credible interval to each relationship determined between each sub-sequence of categories from the query transcript and each of the one or more outcomes. In some examples, the credible interval is determined based on the number and/or proportion of the subset of transcripts containing a matching sub-sequence of categories and which are associated with a given outcome.

For the confidence levels in the analysis which was performed in order to obtain the results shown in FIG. 8, a credible interval was used. A credible interval is a Bayesian concept analogous to but not entirely the same as a confidence interval. A true confidence interval could alternatively be generated. Significance may also be measured, for example by a simple chi-square test against the expected recovery rate.

Where the interaction is a therapy interaction, an outcome may include, e.g. clinical improvement by the patient, recovery by the patient, or engagement by the patient. Clinical improvement as used herein is defined as a patient achieving a statistically significant decrease in symptom severity, as measured on the PHQ-9 and GAD-7 scales. This is the definition used by NHS England in IAPT. Recovery as used herein is defined as the severity of symptoms of a particular patient decreasing to be below the clinical threshold on a clinically suitable scale, such as PHQ-9 or GAD-7. Patient engagement as used herein means the patient completes a minimum number/duration of therapeutic interventions, i.e. does not drop-out of therapy.

The method as a whole may be used in real-time (live) whilst a therapy session is ongoing, or ex post facto after the session has ended.

Sixth Step of the Method

At a sixth step S6, the method ends.

Further Actions That may be Taken

Following steps S1-S6 of the method, further actions may be taken. Suitable further actions will depend on the nature of the interaction from which the transcripts are derived.

The further actions may relate to the method, the system or the computer-readable storage medium comprising instructions.

Where the transcripts are derived from therapy sessions, suitable actions may include outputting a prediction of the outcome of the therapy session represented by the query transcript. Outcome may comprise patient recovery, patient improvement or patient engagement. The predicted outcome may be outputted to one or more of e.g. a therapist, a therapy supervisor (e.g. an experienced therapist), a therapist's employer, a healthcare service or a health insurance company. The outcome may be presented via a therapist interface, or to one or more other suitable interface(s).

Furthermore, using the example of therapy transcripts, the insights gained from the determined relationship data may be used to, e.g.:
- inform clinical discovery about what works in therapy;
- calculating appropriate dose, e.g. by observing presenting severity, therapy quality and recovery status the optimal amount and type of therapy for a patient to receive could be identified;
- support clinical supervision and quality assurance by visualising a large quantity of clinical practice in an intuitive fashion;
- support therapist training, for example a therapist can be shown an objective data driven assessment of their own style allowing for consistent positive feedback;
- support clinical decision support tools, by treating a current session as the beginning of a sequence;
- identify the continuation of the current sequence that will maximise patient outcomes;
- suggest the next type of utterance a therapist may want to use with the current patient as a live alert, for example use the identified subsequences could be used to identify when a patient is at risk of disengaging or not recovering and then a suitable intervention could be suggested;

support the development of digital interventions (digital therapeutics, DTx);

etc.

More detail on possible use cases is provided in the sections below.

Automated Therapist Support

Another action may be to provide automated feedback to a therapist on the quality of the therapy session (e.g. likelihood of improvement of the patient), such that one or more actions may be taken by the therapist e.g. alterations to the current therapy session and/or future therapy sessions. The feedback may be provided to the therapist after completion of the therapy session in order that future therapy sessions may be improved, or alternatively/additionally whilst the therapy session is ongoing (real time or live feedback) so that the therapist may elect to change their current behaviour in order to increase the likelihood of the current therapy session having an improved outcome. In this way the quality of the therapy delivered may be improved and the current patient/future patients are more likely to show good clinical outcome (e.g. likelihood of recovery is increased). The method or system may automatically direct the therapist to take actions that are known or expected to result in improvement of the therapy provided.

The outcome may take the form of a live (real-time, or minimally delayed) prediction of outcome based on the previous utterances made by the therapist (agent) and/or patient (client). Confidence scores or credible intervals for the prediction may also be provided. The feedback may include text and/or graphical representations of the predictions and confidence scores.

The automated feedback provided to the therapist may take the form of an alert. The automated feedback provided to the therapist may suitably take the form of a visual alert, for example a written (text) alert e.g. an automatically-generated email, a pop-up, a text-box or another form of message generated by the therapy system; alternatively/additionally, the visual alert may be for example a graphical alert e.g. a graphical pop-up, a bar chart, pie chart or line chart that e.g. compares the therapist's performance with the average performance. Other suitable alerts may be determined by reference to the particular interface used by the therapist. The alert provided to the therapist may automatically direct the therapist to take one or more actions e.g. suitably to recommend to either increase or decrease (in absolute number or frequency) their provision of utterances belonging to one or more category, or suggest a particular combination of utterance categories (sub-sequence).

Alternatively the therapist may be automatically alerted that their performance appears to be of high quality (e.g. above average outcome is predicted by the method), and they should maintain their current therapy delivery. In that way, the therapist is automatically alerted as to the quality of their performance.

Furthermore, the feedback provided to the therapist on the quality of the therapy delivered may take into account the characteristics of a particular therapy session. For example, by using the current therapy (e.g. CBT) clinical knowledge, session plans can be prepared automatically ahead of each session according to the patient's presenting condition and the chosen treatment model. The session may be monitored while in progress using the system or method, and the therapist may be alerted if the session appears to diverge from the recommended plan.

Automated Quality Assurance

An additional/alternative action that may be taken is to perform automated quality assurance (QA) of therapy sessions. A supervisor may be alerted to below-average delivery of therapy by a therapist (e.g. a prediction of below average likelihood of recovery, based on analysis of the therapy session transcript using the method of the invention). This alert may take the form of e.g. a quality score for a particular therapy session, based on the presence or absence of (or a certain amount or frequency of) particular utterance sub-sequences. Supervisors may be alerted only where a session appears to diverge significantly from expected performance (i.e. where the therapy session meets a predetermined criterion). If the supervisor is thus alerted they may take one or more further action such as more closely monitoring the therapist, advising/supporting the therapist in making improvements, or re-allocating the patient to a different (more suitable) therapist where the therapist performance is particularly poor quality. For example, if the system detects that a therapist is otherwise performing well but is failing to use particular sub-sequences of categories that relate to improved patient outcomes, the system may alert the supervisor that the likelihood of clinical improvement is below average (i.e. the quality of the therapy provided is low) and that the supervisor should recommend to the therapist that more/more frequent sub-sequences of that type should be delivered. Thereby the system provides automated QA and therapy supervision support.

The utterance assignment model is used to provide automated feedback on therapist performance to an entity other than the therapist, for example the therapist's supervisor, the therapist's employer, a therapy service, a healthcare provider or a health insurance company, in order that one or more appropriate actions or interventions may be taken by that entity. This can be considered a type of automated quality assurance. The automated quality assurance may be provided regarding one or more therapy sessions delivered by a particular therapist.

The automated quality assurance is provided either after a particular therapy session has been completed, or alternatively/additionally whilst the therapy session is still taking place (real-time or live automated quality assurance). The automated quality assurance may be provided for all therapy sessions delivered by a particular therapist to a particular patient, in order that changes in the quality of therapy delivered to that patient over time can easily be identified, and one or more appropriate actions or interventions can be taken. Alternatively, the automated quality assurance may be provided for a subset of therapy sessions delivered by a therapist to a particular patient. This subset of therapy sessions may for example be chosen by the supervisor (e.g. the first and every alternate session), or may be randomly selected as part of the automated quality assurance. Alternatively, the automated quality assurance may be provided for a subset of all therapy sessions (e.g. a random sample of therapy sessions) provided by a particular therapist to all of their patients. Alternatively, all therapy session delivered by a particular therapist may be monitored by automated QA (analysis of a therapist's overall performance).

The automated QA may take into account the characteristics of a particular therapy session. For example, by using the current therapy (e.g. CBT) clinical knowledge, session plans can be prepared automatically ahead of each session according to the patient's presenting condition and the chosen treatment model. The session may be analysed using the system or method, and an alert may be generated if the session appears to diverge from the recommended plan.

The actions or interventions that may be taken by the entity (the therapist's supervisor, employer, therapy service, healthcare provider or health insurance company) in response to the automated quality assurance may include providing advice, support or education to the therapist in order that the therapist may improve the quality of the therapy provided, e.g. the identification of areas of potential improvement to be worked on during 1-1 supervision. Alternatively the action or intervention may include reallocating the patient to another therapist of greater experience or increased quality of therapy delivery. In these ways, the quality of care delivered to the patient is increased and therefore the likelihood of the patient improving or recovering is also increased.

By automating the QA, it is possible to provide QA on a greater number of therapy sessions at much reduced cost, thereby introducing the possibility of conducting QA on all therapy sessions. This is beneficial to patients (who are more likely to recover), therapists (who develop their professional expertise) and supervisors (who may therefore focus their expertise where it is most needed.)

Automated Auditing

An additional/alternative action that may be taken is to initiate automated auditing of a therapy service. This involves the automatic collection of a plurality of outputs (outcome predictions) of the method and associated data relating to one or more therapy sessions/one or more therapists, in order that a therapy auditing process may be undertaken by e.g. a therapy service, a health insurance company, an employer, other payer of multiple instances of therapy, a health institution or a state or government body. The plurality of outputs (output predictions) may be anonymised with respect to the patients and/or the therapists. The automated audit may be used to compare e.g. therapy outcomes between different therapists or at different timepoints

Automated Medical Diagnosis

An additional/alternative action that may be taken is to provide automated medical diagnosis. The medical diagnosis relates to the one or more patient taking part in the therapy session. The medical diagnosis may be provided to the therapist, a supervisor of the therapist, a service to which the therapist belongs and/or the payer for the therapy for example an employer, health service or health insurer. The medical diagnosis comprises providing a prediction of the presence of a mental health disorder in the one or more patient, wholly or in part based on analysis of the patient utterances. Additional further actions may be taken by the system subsequent to provision of the medical diagnosis, such as recommendation of a particular therapy protocol to the therapist. In that way, the therapy delivered to the patient, and therefore the likely outcome for the patient, may be improved.

Automated Data Collection

An additional/alternative action that may be taken is to perform automated data collection. This involves the automatic collection of data from any stage of the method including the transcript (text data), the utterances, the sequence of utterances, the sequence of categories, the optional additional inputs and/or the sub-sequences. The data may be collected and stored by the system using any suitable method. The data collected can be used at a later stage to conduct research, further therapy product development, or kept for regulatory, quality assurance or auditing purposes.

EXAMPLES

Example 1

A method was developed to use deep-learning to automatically assign a semantic representation (meaning) to therapy transcript utterances by categorization (classifying each utterance as corresponding to one or more categories from a predetermined list of categories). Categories may also be termed features. Transcripts representing approximately 90,000 hours of internet-enabled CBT were obtained.

Materials and Methods

Experimental Design

All data were obtained from patients receiving IECBT for the treatment of a mental health disorder, between June 2012 and March 2018. IECBT was delivered using a commercial package, originally developed for and currently used in the English National Health Service, provided by Ieso Digital Health (http://uk.iesohealth.com), following internationally recognised standards for information security (ISO 27001; https://www.iesohealth.com/en-gb/legal/iso-certificates). NICE approved disorder specific CBT treatment protocols, based on Roth and Pilling's CBT competences framework, were delivered in a secure online therapy room via instant synchronous messaging, by a qualified CBT therapist accredited by the British Association for Behavioural & Cognitive Psychotherapies (BABCP). Patients (clients) self-referred or were referred by a primary healthcare worker directly to the service. All patients who referred to the service and were suitable (over 18 years old, registered with a GP and not at significant risk of suicide) were offered treatment. Each treatment session was scheduled for a duration of one hour.

The Improving Access to Psychological Therapies (IAPT) programme is a large-scale initiative aimed at increasing access to evidence-based psychological therapy for common mental health disorders within the English National Health Service, whilst controlling costs. IAPT adopts a stepped care approach where patients are offered different psychological therapies based on illness severity. Only patients receiving step 3 treatment (moderate to severe symptoms) were included. At registration patients agree to the services' terms and conditions, including use of anonymized data for audit purposes and to support research, including academic publications or conference presentations.

Therapy Utterance Categories

A total of 33 categories (see Table 8) were defined based on the structure and components of the standard CBT protocol, informed by the CBT competences framework and the Revised Cognitive Therapy Scale (CTS-R). A research psychologist annotated 290 hours of therapy (11,221 utterances) using the 28 agent utterance categories, under the guidance of a qualified clinical therapist, and was blind as to the outcome of each case. For the client categories, four raters tagged 100 randomly selected transcripts each, with 20 transcript overlap used to evaluate interrater agreement (340 hours of therapy in total). Each therapist utterance was therefore tagged with one of 28 'Agent' categories, and each patient utterance was tagged with one of 5 'Client' categories, thereby totaling 33 utterance categories.

A list of all the utterance categories used in the annotation are shown in Table 1 with descriptions and examples of some categories provided in Table 2.

TABLE 1

| Utterance categories applied to transcripts by the deep learning utterance tagging model | |
| --- | --- |
| Agent utterance categories | Client utterance categories |
| Agent: alliance_empathy | Client: change_talk_active |
| Agent: alliance_encouragement | Client: change_talk_exploration |
| Agent: alliance_thanks | Client: counter_change_talk |
| Agent: arrange_next_session | Client: describing_problems |
| Agent: behavioural_reattribution | Client: follow_neutral |
| Agent: bridge | |
| Agent: change_mechanisms | |

TABLE 1-continued

| Utterance categories applied to transcripts by the deep learning utterance tagging model | |
| --- | --- |
| Agent utterance categories | Client utterance categories |
| Agent: cognitive_reattribution | |
| Agent: collaboration | |
| Agent: conceptualisation | |
| Agent: eliciting_feedback | |
| Agent: giving_feedback | |
| Agent: goodbyes | |
| Agent: greeting | |
| Agent: mood_check | |
| Agent: obtain_update | |
| Agent: other | |
| Agent: perceptions_of_change | |
| Agent: planning_for_future | |
| Agent: psychoeducation | |
| Agent: review_homework | |
| Agent: risk_check | |
| Agent: set_agenda | |
| Agent: set_goals | |
| Agent: setting_homework | |
| Agent: skill_teaching | |
| Agent: socratic_questioning | |
| Agent: summarising_session | |

TABLE 2

| Exemplary utterance categories used in transcript annotation. | | |
| --- | --- | --- |
| Category | Description | Example |
| Agent: greeting | An initial greeting welcoming the patient to the session. | "Good morning" |
| Agent: mood_check | Assessing the patient's mood. | "How are you feeling?" |
| Agent: obtain_update | Determining if there have been any changes/issues that have arisen since the last session. | "How have things been since we last spoke?" |
| Agent: bridge | Briefly summarising the most important issues covered in the previous session. | "So, in the last session we talked about . . ." |
| Agent: risk_check | Assessing if patient is at risk of suicide/self-harm. | "I see from your questionnaire that you are having some thoughts of self-harm - is that correct?" |
| Agent: set_agenda | Deciding and prioritizing the topic(s) to discuss during the therapy session. | "What issues would you like us to focus in today's session?" |
| Agent: review_homework | Reviewing and discussing patient's previous homework assignment. | "Did you manage to complete the thought diary I sent you last week?" |
| Agent: set_goals | Setting patient's long-term goals for therapy. | " What would you like to set as your goals from therapy?" |
| Agent: conceptualisation | Conceptualisation is used to help the patient gain an appreciation of the history, triggers and maintaining features of their problem. Includes eliciting historical data, establishing links between the patient's thoughts, feeling, physical symptoms and behaviours. | "The worry leads to the churning in your stomach which causes you to think you are going to be sick" |
| Agent: giving_feedback | Briefly summarising what the patient has said/feedback based on previous utterances. | "It sounds like you've been under a lot of stress at work and you feel this is having an effect on your relationship" |
| Agent: change_mechanisms | Cognitive and behavioural strategies employed by the therapist designed to promote therapeutic change. | "What is the evidence that makes you think this belief is true?" |
| Agent: perceptions_of_change | Discuss what patients feel they have learnt from therapy. | "What do you feel has helped you most during our time together?" |
| Agent: Cognitive_reattribution | Cognitive change methods relate to the thoughts, beliefs and assumptions of a patient. | "I'd like you to write down your thoughts in a diary" |

TABLE 2-continued

Exemplary utterance categories used in transcript annotation.

| Category | Description | Example |
|---|---|---|
| | Includes techniques such as recording thoughts, restructuring beliefs, identifying particular worries. | |
| Agent: Behavioural_reattribution | Behavioural techniques used to modify automatic thoughts and assumptions. Includes techniques such safety seeking or avoidance behaviour, scheduling pleasant activities, graded exposure. | "I want you to make time each evening to sit down and watch your favourite TV show" |
| Agent: Psychoeducation | Psychoeducation involves helping the patient understand their problems within the context of a CBT model. Includes informing the patient about the nature of the physical symptoms they may be experiencing, reducing the patient's belief that they are abnormal. | "Everyone experiences unwanted thoughts, this is perfectly normal" |
| Agent: Skill_Teaching | Skill teaching involves helping the patient focus on, develop and practice new skills. Includes relaxation, problem solving training, skills to prevent them from engaging in ritual behaviours. | "I want you to take a long, deep breath and hold it" |
| Agent: setting_homework | Setting a homework task for the patient. | "I'd like you to keep a diary of anxious predictions for homework" |
| Agent: planning_for_future | Asking the patient how they plan to deal with future issues following completion of therapy. | "What do you think you can continue to do to prevent a future setback?" |
| Agent: eliciting_feedback | The therapist asks the patient for feedback on session/additional questions. | "How have you found today's session?" |
| Agent: summarising_session | A final summary of the day's session focusing on the most important aspects of the discussion. | "So, in today's session we talked about . . ." |
| Agent: arrange_next_session | Arranging time and date of next appointment. | "Would you like to book another appointment for 10.00am next Thursday?" |
| Agent: goodbyes | Saying goodbye at the end of the session. | "Bye for now, and have a good week" |
| Agent: socratic_questioning | Questions used to uncover the assumptions and evidence that underpin people's thoughts | "Why did that make you feel angry? |
| Agent: alliance_thanks | Therapist shows gratitude to patient | "Thanks for sharing" "Thank you for completing . . ." |
| Agent: alliance_empathy | Therapists empathises with patient | "I'm sorry to hear that" "That must have been awful" |
| Agent: alliance_encouragement | Therapist praises patient | "Well done" "That's great" |
| Agent: collaboration | Examples of collaborative processes between therapist and patient | "Why don't we decide on that together?" |
| Agent: other | Miscellaneous utterances not covered by the above categories. | "Have you been to see the GP about your cough?" |

Therapy Insights Model

A deep learning model was developed to automatically classify each utterance into one or more of the 33 categories. Firstly, word2vec (T. Mikolov, I. Sutskever, K. Chen, G. Corrado, J. Dean, Distributed Representations of Words and Phrases and their Compositionality. Adv. Neural Inf. Process. Syst. 26, 3111-3119 (2013) was used on a preprocessed version of the entire data set of over 90,000 hours of therapy session transcripts (approx. 200M words) to learn word embeddings that are suited to the domain of psychotherapy. The data was preprocessed by tokenizing according to whitespace and punctuation and then by lower-casing all tokens (punctuation symbols were kept as separate tokens). This resulted in a vocabulary of 89,260 words, each represented as a continuous dense vector of length 200.

Each utterance was modelled in a transcript as a sequence of word embeddings and fed into a bidirectional long short-term memory (BiLSTM). Max-pooling over the hidden states of the BiLSTM was used to encode each utterance as a fixed-length vector. In order to model each utterance in the context of the entire transcript, each of the fixed-length utterance representations in a transcript was fed into another BiLSTM and the hidden state at each time-step was used to feed into the final output layer. For both of the BiLSTM stages, a hidden dimension of 400 and dropout of 0.5 was used. The output layer mapped each fixed length utterance-in-context representation into a vector of length 32 (32 classes, with the 'Other' class modelled as all zeros) and used a sigmoid activation function on the output. Conceptually, each category was modelled as a binary classifier.

Using the annotated data, a deep learning model was trained using 8,859 utterances from 230 therapy sessions. The use of a neural network that uses a long short-term memory (LSTM) unit over the word embeddings in each utterance, and over the utterances in each transcript, enabled the model to use contextual cues in the overall transcript when classifying any particular utterance (e.g. setting an agenda is more likely to occur early in a session).

After training the deep learning model on 230 transcripts, another 30 transcripts were used to tune hyperparameters (i.e. embedding length, hidden dimension size, dropout probability, and choice of pooling) and the remaining 30 transcripts were used to report the test results.

The deep learning model was then used to classify the utterances relating to over 200,000 hours of therapy transcripts, in order to generate sequences of categories derived from each transcript.

Sequence Matching Algorithm

The Smith Waterman Algorithm (Smith and Waterman, 1981, 'Identification of Common Molecular Subsequences', J Mol Biol, 147, 195-197) is an example of a fuzzy sequence matching algorithm. It is a local sequence alignment algorithm, meaning it finds matching subsequences rather than the commonalities of a pair of whole sequences. It is commonly used for analyzing local similarities (homologies) between nucleic acid or amino acid sequences, and is the general and complete case of a number of heuristic optimisations such as BLAST (Basic Local Alignment Search Tool).

Clinical Outcomes

Clinical outcome was measured in terms of patient recovery. Recovery as used herein is defined as the severity of symptoms of a particular patient decreasing to be below the clinical threshold on a clinically suitable scale, such as PHQ-9 or GAD-7. PHQ-9 and GAD-7 are severity measures corresponding to depressive and anxiety symptoms respectively. Both measures were completed by the patient at initial assessment and before every therapy session. The PHQ-9 is a 9-item measure designed to facilitate screening and severity assessment of depression. According to IAPT, a patient scoring 10 or more in the PHQ-9 (range 0-27) is considered to be suffering from clinically significant depressive symptoms. The GAD-7 is a 7-item screening and severity measure for generalised anxiety disorder. According to IAPT, a patient scoring 8 or more in the GAD-7 (range 0-21) is considered to be suffering from clinically significant anxiety symptoms. If a patient scored 10 or above for PHQ-9 and/or 8 or above for GAD-7 they were classed as meeting the clinical threshold at assessment. Recovery is based on a patient going below the clinical threshold for both PHQ-9 and GAD-7. Patient engagement means the patient completes a minimum number/duration of therapeutic interventions, i.e. does not drop-out of therapy. It can therefore be considered the inverse of patient drop out.

Implementation Methodology

Database
A database was made of all transcripts available that were taggable (classifiable into categories). These were tagged then stored in Azure storage and made available to a serverless supercomputer FIGS. 5 and 7 are different graphical representations of a transcript of a therapy session segmented into utterances, each utterance having been classified as corresponding to one or more category by a deep-learning model.

A serverless supercomputer was constructed on Azure using C# implementation of Smith-Waterman. A single request creates many sub-requests which branches efficiently scaling up and down the compute resource without large standing or capital costs.

An optimization was made to only recalculate changed regions of the scoring matrix on successive matches.

For each query sequence analysed the implementation calculates all matches in a defined subset of the database. The frontend sends subsets of the database as requests in until the whole database has been searched. The serverless supercomputer returns the results as a JSON blob with the number of matches (sub-sequences) at each point in the query sequence and how many of them match recovered patients as well as how many of them drop out on the next session. This therefore provides a relationship between each sub-sequence and outcome, e.g. recovery and/or engagement (engagement being inversely related to drop out).

In addition to sub-sequence matches and outcome (e.g. recovery and/or drop out) correlations, the categories in order are returned to allow for interactive interrogation of the data.

BLOSUM Matrix
A BLOSUM (BLOcks SUbstitution Matrix) matrix is used to attempt to identify the evolutionary importance of the substitution of one amino acid with another in a polypeptide sequence. An attempt to use one based solely on rarity of tags was undertaken but it did not improve the legibility of the recovery rate graph for these example data and parameters.

Graphing
The serverless supercomputer was driven by a Javascript React frontend. It runs the query using several hours of compute time but across many nodes. The data is progressively returned and rendered into a set of D3 charts. This enables a relatively interactive consumption of the data.
Three charts were drawn for each therapy session transcript. One is the raw number of sub-sequence matches at each location in the transcript. This was calculated by counting how many matches include that utterance tag (category).

FIG. 7 is a bar chart showing match counts determined by a Smith Waterman local sequence alignment algorithm for each utterance category present in a query transcript (represented below the bar chart in a graphical representation similar to that of FIG. 4). FIG. 8 is a graph showing the association between the presence of utterance category sub-sequences and clinical response to treatment (outcome).

Example 2

Dose-Response Associations in Psychotherapy Delivery

The dose-response relationship between the total quantity of one-to-one psychotherapy delivered to a patient and their chance of clinical recovery was determined (FIG. 9). The data shown represent 41,485 patients. The inclusion criteria were that all patients started treatment at caseness and have been discharged from treatment, having received a range in the number of therapy sessions from 0 up to 14. The total number of sessions of therapy delivered (where number of sessions is an integer between 0 and 14) was correlated with mean recovery for all patients who received that number of sessions. Recovery rate increased up to about approximately 6-7 sessions of therapy received; the recovery rate reduced for patients where the number of sessions of therapy was greater than 7.

Example 3

Dose-Response Associations in Psychotherapy Delivery—Therapy Component Dosage

The dose-response association between the dose of 'change methods' delivered to a patient and their chance of clinical recovery was determined (FIG. 10). The data shown represent 26,486 patients and 116,635 therapy sessions. The inclusion criteria were that all patients were at caseness, over 18 years of age, were being treated at Step 3 or above, and had completed treatment. Therapy transcripts relating to those patients were segmented into utterances as described above in Example 1. The utterance assignment model (therapy insights model) as described above was used to classify each utterance as corresponding to one or more categories from the predetermined list of categories. For each patient, all utterances classified within the 'Agent: change_mechanisms' category (Table 1) were selected ('Agent:change_mechanisms' utterances correspond with 'change methods'). For each patient, the total number of words present across all utterances classified within the 'Agent:change_mechanisms' category across all treatment sessions (excluding the final session) was calculated ('Number of change methods (words)'). The number of words per feature was deemed to be a more reliable measure of the quantity of a feature than the number of utterances. Patients were then grouped according to the Number of change methods (words) they received (e.g. 0 words, 1-100 words, 101-200 words, 201-300 words etc. to a maximum number of 4300 words). In these groups, the total number of 'Agent: change_mechanisms' words delivered (the 'dose') was correlated with mean recovery for all patients who received that dose of words (FIG. 10). This dose-response profile increases rapidly at lower doses of 'Agent:change_mechanisms' words (up to approximately 1000 words), following which increase slows until a plateau is reached at approximately 3000 words.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

It will further be appreciated by those skilled in the art that although the invention has been described by way of example with reference to several embodiments. It is not limited to the disclosed embodiments and that alternative embodiments could be constructed without departing from the scope of the invention as defined in the appended claims.

The term "comprising" encompasses "including" as well as "consisting" e.g. a composition "comprising" X may consist exclusively of X or may include something additional e.g. X+Y.

The terms "about" or "approximately" in relation to a numerical value x is optional and means, for example, x±10%.

The invention claimed is:

1. A computer-implemented method of determining the dose of psychotherapy delivered during a query psychotherapy interaction, the method comprising:
    receiving a plurality of psychotherapy interaction transcripts and a set of outcome data for each transcript, the outcome data associating each transcript with one or more outcomes;
    receiving a query psychotherapy interaction transcript;
    processing the query transcript and each transcript within the plurality of transcripts,
    wherein processing comprises:
        segmenting each transcript into a sequence of utterances;
        classifying, using a hierarchical bidirectional long short-term memory neural network, each utterance as corresponding to one or more categories from a predetermined list of categories; and
        tagging, using a hierarchical bidirectional long short-term memory neural network, each utterance with one or more of the categories such that each transcript is readable as a sequence of categories;
    comparing, using a fuzzy sequence matching algorithm, the sequence of categories representing the query transcript with the sequences of categories each representing one of the plurality of transcripts, to identify a subset of the sequences of categories representing the plurality of transcripts that contain one or more subsequences of categories which meet a threshold similarity criterion with respect to one or more sub-sequences of categories contained in the sequence of categories representing the query transcript; and
    determining a relationship between each of the one or more sub-sequences of categories contained in the sequence of categories representing the query transcript and an outcome, based on the outcome data associated with the transcripts relating to the identified subset of the sequences of categories representing the plurality of transcripts; and
    determining the dose of psychotherapy delivered during the query psychotherapy interaction by combining the outcomes relating to the one or more sub-sequences relating to the query transcript.

2. A computer-implemented method providing an automated medical diagnosis, the method comprising:
    receiving a plurality of transcripts and a set of outcome data for each transcript, the outcome data associating each transcript with one or more outcomes;
    receiving a query transcript from a patient;
    processing the query transcript and each transcript within the plurality of transcripts, wherein processing comprises:
        segmenting each transcript into a sequence of utterances;
        classifying, using a hierarchical bidirectional long short-term memory neural network, each utterance as corresponding to one or more categories from a predetermined list of categories; and tagging, using a hierarchical bidirectional long short-term memory neural network, each utterance with one or more of the categories such that each transcript is readable as a sequence of categories;

comparing, using a fuzzy sequence matching algorithm, the sequence of categories representing the query transcript with the sequences of categories each representing one of the plurality of transcripts, to identify a subset of the sequences of categories representing the plurality of transcripts that contain one or more sub-sequences of categories which meet a threshold similarity criterion with respect to one or more sub-sequences of categories contained in the sequence of categories representing the query transcript; and determining a relationship between each of the one or more sub-sequences of categories contained in the sequence of categories representing the query transcript and one or more outcomes, based on the outcome data associated with the transcripts relating to the identified subset of the sequences of categories representing the plurality of transcripts; and using the relationship determined to provide a prediction of the presence of a mental health disorder in the patient.

3. The method of claim 1, wherein the fuzzy sequence matching algorithm is a local sequence alignment algorithm.

4. The method of claim 3, wherein the local sequence alignment algorithm is a Smith Waterman Local Alignment algorithm.

5. The method of claim 4, wherein the sub-sequences of categories contained in the sequence of categories representing the query transcript are obtained by generating a scoring matrix between the sequence of categories representing the query transcript and the sequences of categories each representing one of the plurality of transcripts.

6. The method of claim 5, wherein the threshold similarity criterion is met if a sub-sequence of categories contained in the sequence of categories representing the query transcript and a sub-sequence of categories contained in one of the sequences of categories representing the plurality of transcripts produce a score in the scoring matrix which is equal to or greater than a predetermined cutoff score.

7. The method of claim 5, further comprising:
setting one or more parameters to define a manner in which the scoring matrix is generated, the one or more parameters comprising one or more of a match score, a mismatch cost, and a gap cost.

8. The method of claim 3, wherein the local sequence alignment algorithm is a basic local alignment search tool (BLAST) algorithm.

9. The method of claim 8, wherein the sub-sequences of categories contained in the sequence of categories representing the query transcript are obtained by dividing the sequence of categories representing the query transcript into overlapping n-grams, each n-gram comprising n categories.

10. The method of claim 1, wherein determining the relationship comprises determining a strength of correlation or anti-correlation between each sub-sequence of categories contained in the sequence of categories representing the query transcript and each of the one or more outcomes.

11. The method of claim 1, further comprising:
assigning a credible interval to the relationship determined between each sub-sequence of categories contained in the sequence of categories representing the query transcript and each of the one or more outcomes;

wherein the credible interval is determined based at least in part on the number and/or proportion of the sequences of categories representing the plurality of transcripts that contain each sub-sequence of categories and that are associated with each of the one or more outcomes.

12. The method of claim 1, further comprising:
classifying the one or more sub-sequences of categories from the query transcript as effective therapy or ineffective therapy, based on the relationships that are determined.

13. The method of claim 1, further comprising:
assessing the dose of therapy for the query transcript based on the relative frequency of sub-sequences classified as effective and ineffective.

14. A system configured to analyse transcript data, comprising:
a processing unit;
a memory unit; and
a computer-readable storage medium comprising instructions which, when executed by the processing unit, cause the processing unit to:
receive a plurality of transcripts and a set of outcome data for each transcript, the outcome data associating each transcript with one or more outcomes;
receive a query transcript;
process the query transcript and each transcript within the plurality of transcripts by:
segmenting each transcript into a sequence of utterances; and
classifying, using a hierarchical bidirectional long short-term memory neural network, each utterance as corresponding to one or more categories from a predetermined list of categories; and
tagging, using a hierarchical bidirectional long short-term memory neural network, each utterance with one or more of the categories such that each transcript is readable as a sequence of categories;
compare, using a fuzzy sequence matching algorithm, the sequence of categories representing the query transcript with the sequences of categories each representing one of the plurality of transcripts, to identify a subset of the sequences of categories representing the plurality of transcripts that contain one or more sub-sequences of categories which meet a threshold similarity criterion with respect to one or more sub-sequences of categories contained in the sequence of categories representing the query transcript; and
determine a relationship between each of the one or more sub-sequences of categories contained in the sequence of categories representing the query transcript and one or more outcomes, based on the outcome data associated with the transcripts relating to the identified subset of the sequences of categories representing the plurality of transcripts.

15. The system according to claim 14, wherein the predetermined list of categories comprises categories relating to types of therapeutic dialogue.

16. The system according to claim 14, wherein the one or more outcomes include one or more of: patient recovery, patient improvement and patient engagement.

17. The system according to claim 14, wherein the transcript data comprises a transcript of an interaction between a therapist and a patient for one or more therapy sessions.

18. The system according to claim 14, wherein the transcript data is therapy transcript data, preferably psychotherapy transcript data.

19. The system according to claim 14, wherein the transcript data is gathered by one or more of: recording a written conversation between two or more parties, translating a spoken conversation to a textual form using speech recognition software.

20. The method according to claim 2, further comprising providing a recommendation of a therapy protocol based on the automated medical diagnosis.

21. The method according to claim 1, further comprising determining the dose of psychotherapy delivered in a subsequent therapy.

* * * * *